Figure 1A:
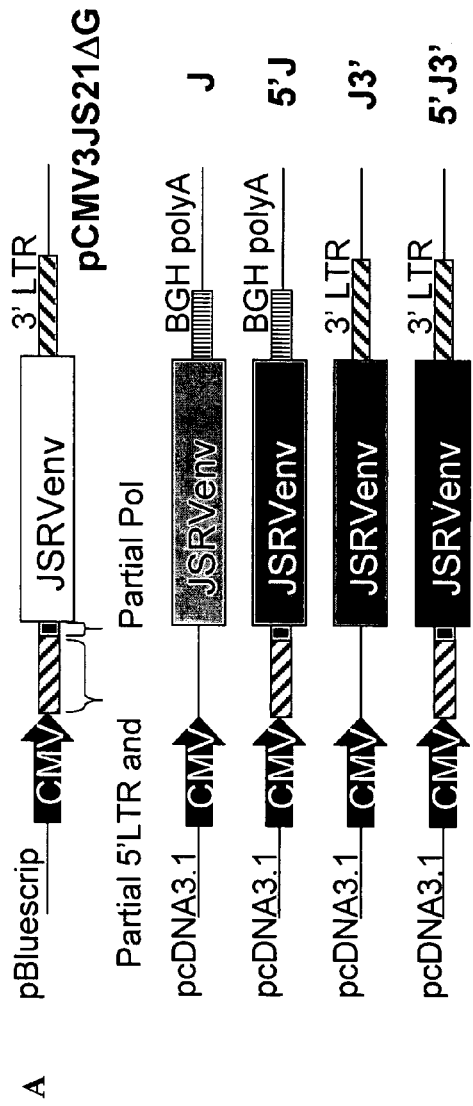

(12) United States Patent
McCray et al.

(10) Patent No.: US 7,608,449 B2
(45) Date of Patent: Oct. 27, 2009

(54) METHODS AND COMPOSITIONS RELATED TO HIGH-TITER PSEUDOTYPED RETROVIRUSES

(75) Inventors: Paul McCray, Iowa City, IA (US); Hung Fan, Laguna Beach, CA (US); Patrick Sinn, Iowa City, IA (US)

(73) Assignees: The Regents of the University of California, Oakland, CA (US); The University of Iowa Research Foundation, Iowa City, IA (US)

( * ) Notice: Subject to any disclaimer, the term of this patent is extended or adjusted under 35 U.S.C. 154(b) by 872 days.

(21) Appl. No.: 10/845,253

(22) Filed: May 13, 2004

(65) Prior Publication Data

US 2004/0265798 A1 Dec. 30, 2004

Related U.S. Application Data

(60) Provisional application No. 60/470,326, filed on May 14, 2003.

(51) Int. Cl.
*C12N 15/00* (2006.01)
*C12N 7/00* (2006.01)
(52) U.S. Cl. .................. 435/320.1; 435/235.1
(58) Field of Classification Search ............... None
See application file for complete search history.

(56) References Cited

U.S. PATENT DOCUMENTS

| | | | |
|---|---|---|---|
| 5,432,260 A | 7/1995 | Stahl | 530/322 |
| 5,643,756 A | 7/1997 | Kayman et al. | 435/69.7 |
| 5,693,509 A | 12/1997 | Cotten et al. | 435/172.3 |
| 5,849,718 A | 12/1998 | Grosveld | 514/44 |
| 5,871,727 A | 2/1999 | Curiel | 424/93.2 |
| 5,902,584 A | 5/1999 | Nicholson et al. | 424/143.1 |
| 6,440,730 B1 | 8/2002 | Von Laer et al. | 435/325 |
| 6,531,123 B1 | 3/2003 | Chang | 424/93.2 |
| 2003/0104357 A1 | 6/2003 | Rai et al. | 435/5 |

FOREIGN PATENT DOCUMENTS

| WO | WO 98/07408 | 4/1998 |
|---|---|---|
| WO | WO 01/04266 | 1/2001 |

OTHER PUBLICATIONS

Johnson J. et al. "Minimum Requirements for Efficient Transduction of Dividing and Nondividing Cells by Feline Immunodeficiency Virus Vectors" J. Virol. 1999 73: 4991-5000.*
Alberti et al., "Envelope-induced cell transformation by ovine betaretroviruses," *J. Virol.*, 76(11):5387-5394, 2002.
Boyes and Bird, "DNA methylation inhibits transcription indirectly via a methyl-CpG binding protein," *Cell*, 64:1123-1134, 1991.
Burns et al., "Vesicular stomatitis virus G glycoprotein psuedo typed retroviral vectors: concentration to very high titer and efficient gene transfer into mammalian and nonmammalian cells," *Proc. Natl. Acad. Sci., USA*, 90:8033-8037, 1993.
Challita et al., "Multiple modifications in *cis* elements of the long terminal repeat of retroviral vectors lead to increased expression and decreased DNA methylation in embryonic carcinoma cells," *J. Virol.*, 69(2):748-755, 1995.
Coil et al. "Jaagsiekte sheep retrovirus env protein stabilizes retrovirus vectors against inactivation by lung surfactant, centrifugation, and freeze-thaw cycling," *J. Virol.*, 75(18):8864-8867, 2001.
Cosset et al., "High-titer packaging cells producing recombinant retroviruses resistant to human serum," *J. Virol.*, 69(12):7430-7436, 1995.
Cousens et al., "Complete sequence of enzootic nasal tumor virus, a retrovirus associated with transmissible intranasal tumors of sheep," *J. Virol.*, 73(5):3986-3993, 1999.
Dirks et al., "Mechanism of cell entry and transformation by enzootic nasal tumor virus," *J. Virol.*, 76(5):2141-2149, 2002.
GenBank Accession No. AF105220.
GenBank Accession No. NC_001494.
Gilliland et al., "Antibody-directed cytotoxic agents: Use of monoclonal antibody to direct the action of toxin A chains to colorectal carcinoma cells," *Proc. Natl. Acad. Sci., USA*, 77(8):4539-4543, 1980.
Goldman et al., "Lentiviral vectors for gene therapy of cystic fibrosis," *Human Gene Therapy*, 8:2261-2268, 1997. (Abstract).
Gordon and Anderson, "Gene therapy using retroviral vectors," *Curr. Opin. Biotechnol.*, 5:611-616, 1994.
Hara et al., "Receptor-mediated transfer of pSV2CAT DNA to mouse liver cells using asialofetuin-labeled liposomes," *Gene Ther.*, 2(10):784-788, 1995.
Jeffers et al., "Covalent modification of the Ebola virus glycoprotein," *J. Virol.*, 76(24):12463-12472, 2002.
Joh

OTHER PUBLICATIONS

Lam et al., "Improved gene transfer into human lymphocytes using retroviruses with the gibbon ape leukemia virus envelope," *Human Gene Therapy*, 7:1415-1422, 1996.

Lever, "HIV and other lentivirus-based vectors," *Gene Therapy*, 3:470-471, 1996.

Liu et al., "Jaagsiekte sheep retrovirus envelope efficiently pseudotypes human immunodeficiency virus type 1-based lentiviral vectors," *J, Virol.*, 78(5):2642-2647, 2004.

Loh et al., "Negative regulation of retrovirus expression in enbryonal carcinoma cells mediated by an intragenic domain," *J. Virol.*, 62:4086-4095, 1988.

Maeda et al., "A minimum c-erbB-2 promoter-mediated expression of herpec simplex virus thymidine kinase gene confers selective cytotoxicity of human breast cancer cells to ganciclovir," *Cancer Gene Therapy*, 8(11):890-896, 2001.

Maeda et al., "Direct transformation of rodent fibroblasts by jaagsiekte sheep retrovirus DNA," *Proc. Natl. Acad. Sci., USA.* ;98(8):4449-54, 2001.

Maeda et al., "Transformation of mouse fibroblasts by jaagsiekte sheep retrovirus envelope does not require phoshatidylinositol 3-kinase," *J. Virol.*, 77(18):9951-9959, 2003.

Markowitz et al., A safe packaging line for gene transfer: Separating viral genes on two different plasmids. *J. Virol.*, 62:1120-1124, 1988.

Miller and Buttimore, "Redesign of retrovirus packaging cell lines to avoid recombination leading to helper virus production," *Mol. Cell Biol.*, 6(8):2895-2902, 1986.

Miller and Chen, "retrovirus packaging cells based on 10A1 murine leukemia virus for production of vectors that use multiple receptors for cell entry," *J. Virol.*, 70:5564-5571, 1996.

Miller and Rosman, "Improved retroviral vectors for gene transfer and expression," *Biotechniques*, 7:980-990, 1989.

Miller et al., "Gene transfer by retrovirus vectors occurs only in cells that are actively replicating at the time of infection," *Mol. Cell Biol.*, 10(8):4239-4242, 1990.

Miller et al., "Use of retroviral vectors for gene transfer and expression," *Meth. Enzymol.*, 217:581-599, 1993.

Miller, "Human gene therapy comes of age," *Nature*, 357:455-460, 1992.

Mortiz et al., "Fibronectin improves transduction of reconstituting hematopoietic stem cells by retroviral vectors: Evidence of direct viral binding to chymotryptic carboxy-terminal fragments," *Blood*, 88(3):855-862, 1996.

Nienhuis et al., In: *Viruses and Bone Marrow*, Hematology, Young Ed., 16:353-414, 1993.

Palmarini and Fan, "Retrovirus-induced ovine pulmonary adenocarcinoma, an animal model for lung cancer," *J. National Cancer Institute*, 93(21):1603-1614, 2001.

Palmarini and Fan., "Molecular biology of jaagsiekete sheep retrovirus," *Curr Top Microbiol. Immunol.*, 275:81-115, 2003.

Palmarini et al., "A phosphatidylinositol 3-kinase docking site in the cytoplasmic tail of the jaagsiekte sheep retrovirus transmembrane protein is essential for envelope-induced transformation of NIH 3T3 cells," *J. Virol.*, 75(22):11002-11009, 2001.

Palmarini et al., "Jaagsiekte sheep retrovirus is necessary and sufficient to induce a contagious lung cancer in sheep," *J. Virol.*, 73:6964-6972, 1999.

Palmarini et al., "Spliced and prematurely polyadenylated jaagsiete sheep retrovirus-specific RNAs from infected or transfected cells," *Virology*, 294(1):180-188, 2002.

Rai et al., "Candidate tumor suppressor HYAL2 is a glycosylphosphatidylinositol (GLI)-anchored cell-surface receptor gor jaagsiekte sheep retrovirus, the envelope protein of which mediates oncogenic transformation," *Proc. Natl. Acad. Sci., USA*, 98(8):4443-4448, 2001.

Rai et al., "Retrovirus vectors bearing jaagsiekte sheep retrovirus env transduce human cells by using a new receptor localized to chromosome 3p21.3," *J. Virol.*, 74(10):4698-4704, 2000.

Russell and Miller, "Foamy virus vectors," *J. Virol.*, 70:217-222, 1996.

Sanders, "No false start for novel pseudotyped vectors," *Curr. Opin. Biotech.*, 13:437-442, 2002.

Schwartz et al., "District RNA sequences in the *gag* region of human immunodeficiency virus type 1 decrease RNA stability and inhibit expression in the absence of rev protein," *J. Virol.*, 66:150-159, 1992.

Sharp et al., "Rapid transmission of sheep pulmonary adenomatosis (jaagsiekte) in young lambs," *Arch. Virol.*, 78:89-95, 1983.

Sinn et al., "Lentivirus vectors psuedotyped with filoviral envelope glycoproteins transduce airway epithelia from the apical surface independently of folate receptor alpha," *J. Virol.*, 77(10):5902-5910, 2003.

Spanjer and Scherphof, "Targeting of lactosylceramide-containing liposomes to hepatocytes in vivo," *Biochim. Biophys. Acta*, 734(1):40-47, 1983.

Steffy and Wong-Staal, "Genetic regulation of human immunodeficiency virus," *Microbiol. Rev.*, 55(2):193-205, 1991.

Subbramanian and Cohen, "Molecular biology of the human immunodeficiency virus accessory proteins," *J. Virol.*, 68(11):6831-6835, 1994.

Szyf et al., "A DNA signal from the Thy-1 gene defines de novo methylation patterns in embryonic stem cells," *Mol. Cell Biol.*, 10(8):4396-4400, 1990.

Trono, "HIV accessory proteins: Leading roles for the supporting cast," *Cell*, 82:189-192, 1995.

Wang et al., "Feline immunodeficiency virus vectors persistently transduce nondividing airway epithelia and correct the cystic fibrosis defect," *J. Clin. Invest.*, 104(11):R55-62, 1999.

York et al., "Isolation, identification, and partial cDNA cloning of genomic RNA of jaagsiekte retrovirus, the etiological agent of sheep pulmonary adenomatosis," *J. Virol.*, 65(9):5061-5067, 1991.

* cited by examiner

FIG. 2A-2B

FIG. 7A-7B

METHODS AND COMPOSITIONS RELATED TO HIGH-TITER PSEUDOTYPED RETROVIRUSES

This application claims priority to U.S. Provisional Patent Application Ser. No. 60/470,326, filed May 14, 2003, which is incorporated in its entirety by reference.

This invention was made with government support under grant numbers RO1 HL-61480 and PPG HL-51670 awarded by the National Institutes of Health. The government has certain rights in the invention.

BACKGROUND OF THE INVENTION

I. Field of the Invention

The present invention relates generally to the fields of virology and genetic therapy. More particularly, it concerns coexpressing envelope proteins for producing a high titer pseudotyped viral composition.

II. Description of Related Art

Jaagsiekte sheep retrovirus (JSRV) is the causative agent of a contagious lung cancer of sheep called ovine pulmonary carcinoma or sheep pulmonary adenomatosis (Palmarini et al., 1999). Tumors originate from type II secretory alveolar and nonciliated bronchiolar epithelial cells, and late stages of the disease are accompanied by the secretion of copious lung fluid containing the virus. Purified virus induces multifocal tumors in as little as 10 days (Sharp et al., 1983). JSRV is a simple retrovirus with typical gag, pol, and env genes. The JSRV envelope glycoprotein appears to have transforming properties when it is expressed in certain cell types. The viral structural (gag) and enzymatic (pol) proteins interact primarily with viral components. The envelope (env) protein interacts with cellular components to mediate virus entry. The contagious nature of JSRV and its ability to survive exposure to proteases and surfactants present in lung fluid suggest that vectors based on JSRV might be useful for gene therapy, particularly therapies targeted to the lung, provided that the pathogenic features of the virus can be controlled.

Viral vectors can transduce genes into target cells with high efficiencies via specific virus envelope-host cell receptor interaction and viral mechanisms for gene expression. Consequently, viral vectors have been used as vehicles for the transfer of genes into many different cell types including whole embryos, fertilized eggs, isolated tissue samples, and cultured cell lines. The ability to introduce and express a foreign gene in a cell is useful for the study of gene expression and the elucidation of cell lineages (Watson et al., 1992). Retroviral vectors, capable of integration into the cellular chromosome, have also been used for the identification of developmentally important genes via insertional mutagenesis (Watson et al., 1992). Viral vectors, and retroviral vectors in particular, are also used in therapeutic applications (e.g., gene therapy), in which a gene (or genes) is added to a cell to replace a missing or defective gene, or to provide a therapeutic gene not normally expressed in the infected cell.

In view of the wide variety of potential genes available for therapy, it is clear that an efficient means of delivering these genes is sorely needed in order to fulfill the promise of gene therapy for treating infectious, as well as non-infectious diseases. Several viral systems including murine retrovirus, lentivirus, adenovirus, parvovirus (adeno-associated virus), vaccinia virus, and herpes virus have been developed as therapeutic gene transfer vectors (For review see, Nienhuis et al., 1993).

Factors affecting viral vector usage include tissue tropism, stability of virus preparations, genome packaging capacity, and construct-dependent vector stability. In addition, in vivo application of viral vectors is often limited by host immune responses against viral structural proteins and/or transduced gene products.

The low production of recombinant virus produced by some retroviral system (e.g., $10^6$ transducing units (tu)/ml or lower) compared to the adenoviral system (up to $10^{12}$ particles/ml) means that human cells are infected at a very low efficiency. This low efficiency is particularly problematic when the target cell type is represented at very low numbers in the tissue to be infected. The hematopoietic stem cell is a preferred target for gene therapy in a large number of disorders, these cells are present at very low frequencies. For example, totipotent embryonic stem cells have been reported to occur at a frequency of $10^{-4}$ to $10^{-6}$ in bone marrow (Glick and Pasternak, 1994). Thus, the low titer produced by existing vector systems is highly problematic for stem cell infection, as well as other therapies.

Additional vector systems are needed to provide a means of delivering and expressing genes efficiently in mammalian cells, particularly human cells. Various new methods and compositions are necessary if the promise of gene therapy is to be realized.

SUMMARY OF THE INVENTION

The invention includes methods and compositions for increasing the titer, altering the tropism, and/or increasing the stability of retroviral or other pseudotyped viral preparations. High titer viral preparations of the invention may be used in various therapeutic methods and compositions including, but not limited to the delivery of therapeutic genes. The high titer viral compositions may be used in vitro, ex vivo and/or in vivo for the treatment of various disorders and conditions. High titer viral preparations may be produced by expressing a heterologous env protein in a cell producing viral particles. "Heterologous" as used herein refers to a nucleic acid sequence or amino acid sequence that is an element not normally occurring in a particular nucleic acid, peptide, polypeptide, protein, or virus, unless it is an engineered element. Throughout the specification the designation "env" will refer to an envelope protein, whereas the designation "env" will refer to an envelope gene or nucleic acid. In particular embodiments, the invention includes compositions and methods for producing high titer pseudotyped retrovirus and retroviral vectors.

Certain embodiments include an isolated polynucleotide (pseudotyping expression cassette) comprising a first polynucleotide segment encoding all or part of a env protein and splice acceptor site 5' of the translation initiation codon; a second polynucleotide segment positioned 5' to the first polynucleotide segment comprising all or part of a retroviral 5' LTR and a splice donor site; and a third polynucleotide segment positioned 3' to the first polynucleotide segment comprising all or part of a retroviral 3' LTR; wherein the polynucleotide comprises less than a complete retroviral genome.

The first polynucleotide segment may encode all or part of a Jaaksiekte sheep retrovirus env protein or a modified Jaaksiekte sheep retrovirus env protein. It is also contemplated that the polynucleotide may encode other env proteins. In certain aspects of the invention, the env protein may be a modified env protein.

The second polynucleotide segment may encode all or part of a Jaaksiekte sheep retrovirus 5' LTR or other similar retroviral 5' LTR. The 5' LTR may include R and U5 regions. The 5' LTR will typically include a splice donor site. In certain embodiments, the splice donor site is a retroviral major splice donor site.

The third polynucleotide segment may encode all or part of a Jaaksiekte sheep retrovirus 3' LTR. The 3' LTR may comprises a U3, R, and U5 region. The use of other retroviral 5' and 3' LTRs are also contemplated.

The polynucleotide may also include a promoter controlling expression of the nucleotide sequence encoding an env protein. In certain embodiments the promoter is a CMV IE promoter. The use of other promoters known in the art are also contemplated.

In various embodiments, the polynucleotide comprises an expression cassette, which may or may not be part of an expression vector. In certain aspects, the polynucleotide may or may not be incorporated into the genome of a cell. In certain embodiments, an expression vector or cassette may be maintained episomally in a cell.

Certain aspects of the invention include retroviral packaging cells comprising a pseudotyping expression cassette or polynucleotide comprising a nucleic acid segment encoding a Jaaksiekte sheep retrovirus envelope protein; and a flanking segment positioned 5' and/or 3' to the segment encoding a Jaaksiekte sheep retrovirus envelope protein that comprise all or part of a 5' or 3' LTR of the Jaaksiekte sheep retrovirus. In various embodiments, the pseudotyping expression cassette may comprise a splice donor/acceptor pair positioned 3' to the transcription start site and 5' to the translation start site. The nucleic acid segment may or may not be incorporated into the genome of the cell. The nucleic acid sequence may comprise both the 5' and 3' LTR segments of the Jaaksiekte sheep retrovirus or other similar retrovirus.

In various embodiments, retroviral packaging cells express one or more non-Jaaksiekte sheep retrovirus viral proteins. At various stages, the cell will include and/or shed a pseudotyped virus or viral particle. The virus or viral particle may comprise an expression vector and/or therapeutic agent. In certain aspects, the therapeutic agent is a therapeutic gene or genetic element. The expression vector is typically a non-Jaaksiekte sheep retroviral vector.

In accordance with the present invention, a selected gene or polypeptide may refer to any protein, polypeptide, or peptide. A therapeutic gene or polypeptide is a gene or polypeptide which can be administered to a subject for the purpose of treating or preventing a disease. For example, a therapeutic gene can be a gene administered to a subject for treatment or prevention of cancer. Examples of therapeutic genes include, but are not limited to, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, Bax, Bak, Bik, Bim, Bid, Bad, Harakiri, Fas-L, mda-7, fus, interferon $\alpha$, interferon $\beta$, interferon $\gamma$, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

Further examples of therapeutic genes include the gene encoding carbamoyl synthetase I, omithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, -glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, -L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, $\beta$-endorphin, $\beta$-melanocyte stimulating hormone, cholecystokinin, endothelin I, galanin, gastric inhibitory peptide, glucagon, insulin, lipotropins, neurophysins, somatostatin, calcitonin, calcitonin gene related peptide, $\beta$-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

In certain embodiments of the invention, a composition may comprise a viral particle with all or part of a Jaaksiekte sheep retrovirus envelope protein associated with the virus envelope, wherein the Jaaksiekte sheep retrovirus envelope protein is heterologous to the viral particle, i.e., a JSRV pseudotyped viral particle. The virus may or may not be a retrovirus. A retrovirus of the invention may be a lentivirus, in particular an immunodeficiency virus. In particular embodiments, the retrovirus may be a feline immunodeficiency virus or expression vector. In certain embodiments, the pseudotyped viral particle comprises a therapeutic agent. In particular embodiments, the therapeutic agent is a therapeutic gene or genetic element.

In various embodiments, an env protein, in particular a Jaaksiekte sheep retrovirus env protein, may be a modified env protein. In certain embodiments, the modified env protein comprise a targeting ligand. The targeting ligand may or may not be covalently coupled to the Jaaksiekte sheep retrovirus envelope protein. In some aspects of the invention, a Jaaksiekte sheep retrovirus envelope protein or other envelope protein is an insertionally modified or fusion protein that comprises a targeting peptide and/or amino acid modification that alters the tropism of the pseudotyped viral particle.

Certain embodiments of the invention include methods comprising contacting a cell with a pseudotyping expression cassette and a therapeutic expression vector. The expression cassette may comprise a Jaaksiekte sheep retrovirus env protein coding region and all or part of a 5' and/or a 3' LTR sequence of the Jaaksiekte sheep retrovirus. The method includes obtaining a virus produced by the cell. The expression cassette may or may not be integrated into the genome of the cell. In certain aspects of the invention, at least one protein of the virus is provided by the cell. In certain aspects, the cell is a packaging cell for the therapeutic expression vector. The expression cassette and the viral expression vector may or may not be introduced into the cell simultaneously.

In certain embodiments, a viral composition may be produced by methods comprising contacting a cell with a pseudotyping expression cassette and a therapeutic expression vector. The expression cassette may comprise a Jaaksiekte sheep retrovirus envelope protein coding region and all or part of a 5', a 3' sequence or both a 5' and 3' sequence of the Jaaksiekte sheep retrovirus; and obtaining a virus produced by the cell.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A and 1B. Widely divergent FIV titer conferred by different configurations of the JSRV envelope GP expression cassette. FIV vector expressing nuclear targeted β-galactosidase was prepared by three plasmid transfection and titered by limiting dilution on HT1080 cells as described in Materials and Methods. Five different configurations of the JSRV env GP are shown schematically (FIG. 1A) and the resulting titers are presented as the average transducing units per milliliter (FIG. 1B) (TU/ml)±standard error. The n for each datum set is shown. (*, $p<0.05$ versus J; **, $p<0.01$ versus J).

FIGS. 2A and 2B. Steady state levels of JSRV envelope RNA from J, 5'J, J3' and 5'J3' following transient transfection into 293T cells. (FIG. 2A) Total JSRV RNA levels were determined by RNA dot blot assay and quantified by phosphorimaging. (n=6; , $p<0.01$ versus J). (FIG. 2**B) JSRV RNA was separated into nuclear and cytoplasmic fractions and subjected to dot blot assay and quantified by phosphorimaging (n=6; *, $p<0.05$ versus J; **, $p<0.01$ versus J).

FIGS. 3A-3D. Confirmation and contribution of a splice event. A splice event was confirmed and the splice junctions were determined by 5'RACE of RNA derived from cells transiently transfected with pCMV3JS21ΔGP. (FIG. 3A) The sequence chromatograph of the spliced product is shown. (FIG. 3B) The location of the splice event in the pCMV3JS21ΔGP is shown schematically. The splice junction (donor and acceptor) and the JSRV env start codon are indicated. (FIG. 3C) Vector titer was determined from FIV prepared using either pCMV3JS21ΔGP (n=7) or the identical construct with the exception of a mutation of splice donor (pCMV3JS21ΔGP ΔSD; n=3). (, $p<0.01$). (FIG. 3**D) JSRV RNA from cells transiently transfected with either pCMV3JS21ΔGP or pCMV3JS21ΔGP ΔSD was separated into nuclear and cytoplasmic fractions and subjected to dot blot assay and phosphorimaging. (n=6; *, $p<0.05$.)

FIGS. 4A and 4B. Generation of stable cell lines expressing each of the different JSRV envelope constructs. Flp-recombinase was used to generate single copy/single loci as described in Materials and Methods. (FIG. 4A) A single copy integration event for each cell line was confirmed by determining JSRV env gene copies using real-time PCR amplification of genomic DNA and normalized to GAPDH gene copies. (n=6). (FIG. 4B) Doxycycline responsiveness was confirmed by real-time PCR amplification of JSRV RNA in the presence or absence of 10 μg/ml doxycycline. (n=6; *, $p<0.05$.)

FIG. 5. RNA half-lives of JSRV env RNA expressed from J, 5'J, J3', and 5'J'3'. Half-lives were determined in the established stable cell lines. Cells were stimulated with doxycycline for 24 hours. Following doxycycline treatment, cellular transcription was inhibited by actinomycin D treatment (10 μg/ml). Cells were collected at 6 hour intervals from 0 to 24 hours, total RNA was purified and JSRV env RNA was quantified by real-time PCR.

FIGS. 6A-6C. Steady state levels of JSRV envelope protein from HA-tagged J and pCMV3JS21ΔGP. HA-tagged J and pCMV3JS21ΔGP constructs (FIG. 6A) were transiently transfected into 293T cells along with a mock transfection negative control. 24 hours later lysates were collected and subjected to western blot analysis. Identical blots were probed with either an anti-HA (FIG. 6B) or anti-human actin (FIG. 6C) antibodies. The arrow indicates the 37 KD band of HA-tagged JSRV Env protein corresponding to TM protein.

FIGS. 7A and 7B. FIV vector titers resulting env GP expressed from pIXSL or pcDNA31 (FIG. 7A). An expression plasmid was constructed including the JSRV 5' and 3' regions (pIXSL) and used to express 4 other envelope glycoproteins to generate FIV. Envelope GP expressed from pcDNA3.1 (black bars) or from pIXSL (open bars) (FIG. 7B). The n for each datum set is shown. (*, $p<0.01$).

FIGS. 8A-8D. In vivo gene transfer with JSRV-FIV. Pseudotyped FIV vector was delivered to rabbit airways through a wedged radiopaque catheter. Animals were X-rayed to verify catheter placement (FIG. 8A). Black arrows indicate the position of the catheter. Rabbit lungs were examined by X-gal staining 6 months after instillation of JSRV-FIV (FIG. 8B & FIG. 8C), or saline (FIG. 8D). As indicated by the blue arrow, occasional β-galactosidase positive cells were observed in the alveolar epithelium. Tissue sections were counterstained with nuclear fast red. Scale bars=100 μM.

Figures 9A, 9B:
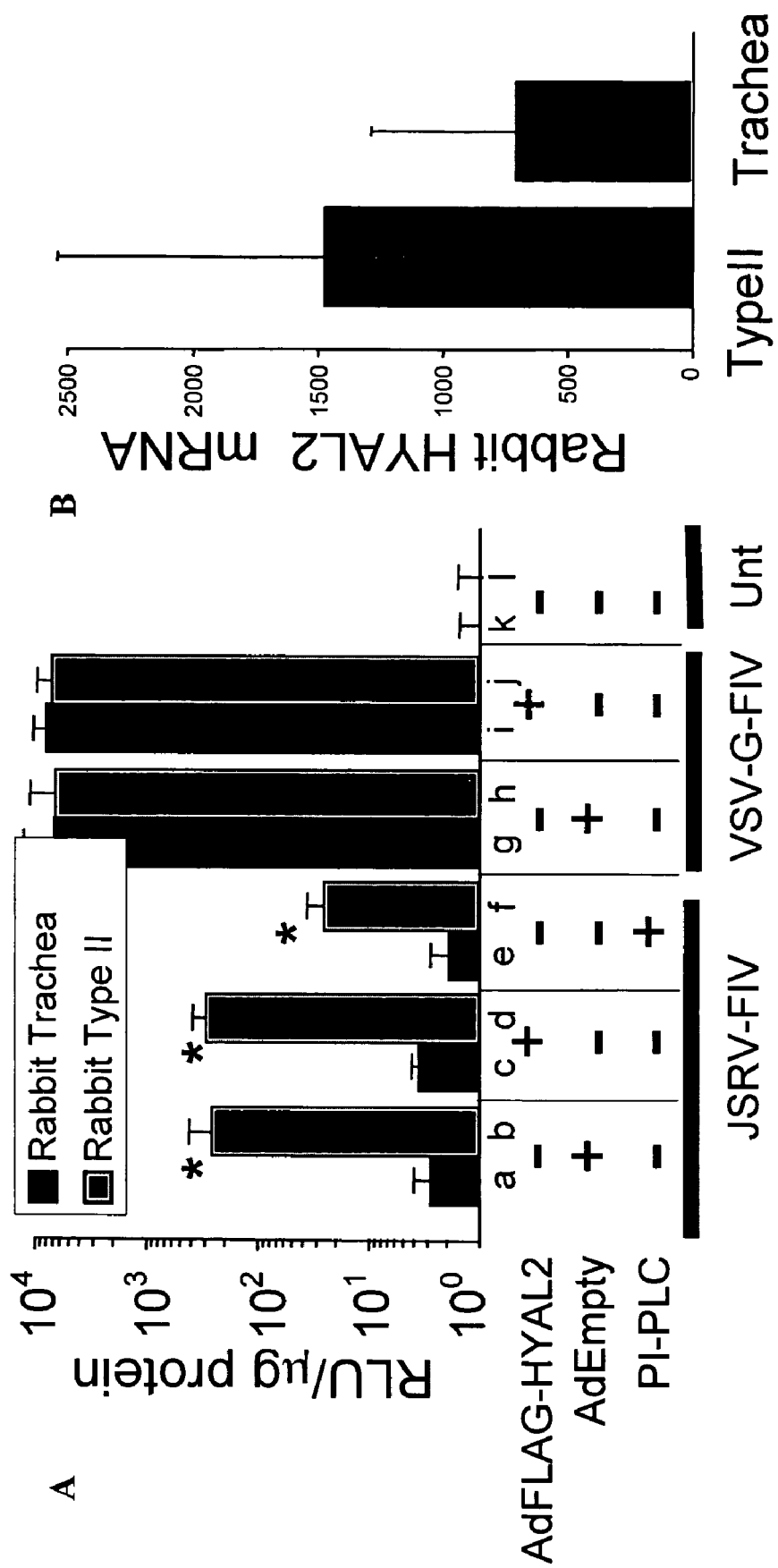

FIGS. 9A and 9B. Transduction levels of primary cultures of non-polarized rabbit airway epithelial cells with pseudotyped FIV vector. Primary rabbit tracheal or type II cells were cultured as described in Materials and Methods. (FIG. 9A) Epithelia were pretreated with AdFLAG-HYAL2, Ad-Empty, or PI-PLC as indicated. After a suitable pretreatment (as described in Materials and Methods), the epithelia were transduced with either JSRV-FIV or VSV-G-FIV at an MOI of 50. Four days after vector incubation, cells were harvested and the β-galactosidase activity was quantified and normalized to total protein. Unt, untreated. (FIG. 9B) Expression levels of rabbit HYAL2 mRNA in the type II and tracheal epithelia primary cultures were quantified by real-time PCR. *, $p<0.05$.

DESCRIPTION OF ILLUSTRATIVE EMBODIMENTS

The invention addresses various limitations of gene delivery vectors. In particular, embodiments of the invention include novel methods and compositions related to making high titer pseudotyped retroviral vector compositions. The term "pseudotyping" or "pseudotyped virus" refers to an enveloped virus that has incorporated into its envelope a heterologous envelope glycoprotein (env or env protein). The heterologous envelope glycoprotein is typically incorporated into the virus during the budding or virus production process. Pseudotyped viruses may have a modified host range that is influenced by the properties of the heterologous envelope glycoprotein. Thus, embodiments of the invention include improved methods and compositions related to pseudotyped retroviruses suitable for ex vivo and in vivo methods including gene transfer and other therapeutic and experimental methods.

Certain embodiments of the invention include pseudotyped retroviral vectors comprising a heterologous envelope glycoprotein derived from a Jaagsiekte sheep retrovirus (JSRV env). Other envelope glycoproteins are contemplated including, but not limited to, envelope glycoproteins of members of the filovirus, retrovirus, rhabdovirus, coronavirus, togavirus and paramyxovirus families. The heterologous envelope glycoprotein may be expressed from a polynucleotide comprising various titer enhancing nucleic acid elements. The titer enhancing elements may be derived from the genome of JSRV, although equivalent regions from other viruses or synthetic versions of the elements are contemplated. One or more of these titer enhancing elements may be operatively coupled to various env genes. Typically, the heterologous env is expressed in a cell that also contains a genome of a second virus that is not the virus from which the heterologous env is derived. The genome of the second virus is able to be packaged into a viral particle. Any additional proteins or nucleic acids needed for viral packaging may be provided by genetic elements integrated into the genome of the cell and/or expressed from episomal genetic elements as is well know to one of skill in the art.

Exemplary titer enhancing elements are illustrated in various herein and include, but are not limited to the (a) 5' LTR including a splice-donor, in particular, the major splice donor site, (b) a splice-acceptor site upstream of the env coding sequence and/or (c) the 3' LTR sequences of the JSRV env including one or more of the 3' U3, R, and U5 regions, which are described herein, positioned 3' to the env coding sequence. One mechanism for enhancing the titer is that these elements alone or together confer an increased stability to the env mRNA. The presence of one or more of the titer enhancing elements in an expression cassette encoding a heterologous envelope glycoprotein (i.e., a JSRV env glycoprotein) confers increased titers of pseudotyped retroviruses. Such an approach for making envelope glycoprotein expression cassettes may be used as a solution to the limitations of low titer and low stability viral compositions. Embodiments of the invention include pseudotyping of any virus that comprises a viral envelop into which a heterologous env may be incorporated. In certain embodiments, the env is derived from JSRV.

A pseudotyped virus of the invention may allow gene transfer and delivery of other therapeutic compositions to various cells, tissue, and/or organs of an organism or patient, e.g., human airway epithelia and/or hepatocytes.

I. Pseudotyped Viruses

Pseudotyped viruses have several experimental and clinical applications. The outer envelope of a virus, through its interaction with a cell surface and/or receptor or other surface molecules, plays a role in determining the tropism of a virus. Pseudotyping a virus can thereby provide it with an expanded or modified tropism for target cells or may restrict it to specific cells that are the object of experimental or therapeutic interest. Further, a pseudotyped virus may have an altered stability and/or interaction with the host that increases its efficacy. One example is the production and/or concentration of pseudotyped viruses to a higher transduction or viral particle titers than a virus with only a native envelope glycoprotein.

Methods of producing pseudotyped viruses include (a) the expression of an env protein in cells capable of packaging and/or producing a viral particle, and (b) introducing into the cell a viral vector or other nucleic acid capable of being packaged into the viral particle. Other components needed for packaging and virus production may be supplied by various means known to one of skill in the art. For example, the cell line may be stably transfected with nucleic acids that provide for the production of proteins or nucleic acids for processing of a viral particle.

A. Retroviral Vectors

The term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is typically referred to as a "provirus." The provirus may serve as a template for RNA polymerase II and direct the expression of RNA molecules which encode the structural proteins and enzymes needed to produce new viral particles. At each end of the provirus are structures called "long terminal repeats" or "LTRs." The LTR contains numerous regulatory signals including transcriptional control elements, polyadenylation signals and sequences needed for replication and integration of the viral genome. These regulatory signals include the U5, R, and U3 regions.

The R Region is a short 18-250 nucleotide (nt) sequence which forms a direct repeat at the both ends of the genome, which is therefore 'terminally redundant'. Transcription typically initiates at the first base of the R region in the 5' LTR, and polyadenylation occurs immediately after the last R region base in the 3' LTR. The primary transcript is typically shorter than the provirus.

The U3 region is a non-coding region of 200-1,200 nt which forms the 5' end of the provirus after reverse transcription and contains the promoter elements responsible for transcription of the provirus. The U3 region includes several features of interest: the integration attachment site (att) at the far 5' end, the promoter TATA box (a segment of DNA, located approximately 19-27 base pairs upstream from the start point of eukaryotic structural genes, to which RNA polymerase binds), and promoter (SP1) regions (promoter binding site for RNA polymerase and reverse transcriptase) among other elements.

The U5 regions is a non-coding region of 75-250 nt which is the first part of the genome to be reverse transcribed, forming the 3' end of the provirus genome. The U5 region contains a polyA downstream element and a second integration attachment site at the 3' end. These are significant only in the 3' LTR.

The major 5' splice donor (SD) site is used for the processing of full-length genomic RNA to subgenomic mRNA for the syntheses of various viral proteins. The major packaging signal (psi, Ψ) serves as a contact point for the Gag nucleocapsid protein to bind the RNA and to incorporate it into virus particles.

There are several genera included within the family Retroviridae, including Cisternavirus A, Oncovirus A, Oncovirus B, Oncovirus C, Oncovirus D, Lentivirus, and Spumavirus. Some of the retroviruses are oncogenic (i.e., tumorigenic), while others are not. The oncoviruses induce sarcomas, leukemias, lymphomas, and mammary carcinomas in susceptible species. Retroviruses infect a wide variety of species, and may be transmitted both horizontally and vertically. They are integrated into the host DNA, and are capable of transmitting sequences of host DNA from cell to cell. This has led to the development of retroviruses as vectors for various purposes including gene therapy.

Retroviral vectors are typically derived from the amphotropic Moloney murine leukemia virus (MLV-A). The amphotropic MLV vector system has been well established and is a popular tool for gene delivery (See e.g., Gordon and Anderson, 1994; Miller et al., 1993).

Other retroviruses, including human foamy virus (HFV) and human immunodeficiency virus (HIV) have gained much recent attention, as their target cells are not limited to dividing cells and their restricted host cell tropism can be readily expanded via pseudotyping, for example, with vesicular stomatitis virus G (VSV-G) envelope glycoproteins (See e.g., Burns et al., 1993; Lever, 1996; Russell and Miller, 1996).

The elements essential to a retroviral vector system, e.g., MLV, are typically viral structural proteins gag, pol and env, the long terminal repeats (LTR), the reverse transcription templates including primer binding site (PBS) and polypurine tract (PPT), and the packaging signals (psi, Ψ). The MLV-A vector system is comprised of a packaging cell line expressing gag, pol and env, and a vector construct containing LTRs, PBS, PPT and the packaging signal sequences. Up to 8 kbp of foreign sequences can be inserted into the MLV vector and packaged into virus particles. The commonly used amphotropic MLV packaging cell lines such as PA317, PG-13, Ψ-CRIP, GP-AM12 and FLY-A13 produce $10^5$-$10^7$ transducing units per ml (TU/ml) after vector DNA transfection (Cosset et al., 1995; Kotani et al., 1994; Lam et al., 1996; Markowitz et al., 1988; Miller and Chen, 1996).

Vector DNA is introduced into a packaging cell by any of a variety of techniques (e.g., calcium phosphate coprecipitation, lipofection, electroporation, etc.). The viral proteins produced by the packaging cell mediate the insertion of the vector sequences in the form of RNA, or DNA in the case of other viral systems, into viral particles which are shed into the culture supernatant. The system may be designed to prevent the production of a replication-competent virus as a safety measure. The recombinant viral particles produced in these systems can infect and integrate into the target cell but cannot spread to other cells. These safeguards may be used to prevent the spread of the recombinant virus from the treated patient and to avoid the possibility of helper virus-induced disease (Miller and Buttimore, 1986; and Markowitz et al., supra). In other aspects the virus may be replication competent or conditionally replicative. In certain embodiments of the invention, a pseudotyping expression cassette of the invention is co-expressed with heterologous viral components to produce a JSRV env pseudotyped virus. For a review of enveloped viruses see Field's Virology, 4th Ed., 2001.

Cell clones expressing the appropriate components (i.e., producer cell clones) can be selected and established. Increased transduction efficiencies may be achieved by modification of the transduction protocols through means such as repetitive infection steps, cocultivation with the producer cell line, centrifugation, and modification of the culture conditions using growth factors and fibronectin, for example (Kotani et al., 1994; Moritz et al., 1996). Packaging cell lines and methods for producing packaging cell lines are well known in the art.

Despite these advantages, existing retroviral vectors, e.g., MLV, are limited by several intrinsic problems: 1) they do not infect non-dividing cells (Miller et al., 1990); 2) they produce only low titers of the recombinant virus (Miller and Rosman, 1989; Miller, 1992); 3) they express foreign proteins at low levels and often get "turned-off" or inactivated after integration (Miller, 1992); 4) the instability of the enveloped virus particles, as it is both difficult to concentrate in vitro and difficult to manipulate in vivo (Miller, 1992); 5) the LTR activity is also known to be suppressed in embryonal cells (Challita et al., 1995; Loh et al., 1988); and 6) long term expression after viral integration is often restricted by transcription repression, likely due to DNA methylation (Boyes and Bird, 1991; Szyf et al., 1990). Certain aspects of the invention address one or more of the limitations and allow the production of additional methods and compositions related to the novel pseudotyped viral particles described herein.

The low production of recombinant virus produced by retroviral system (e.g., $10^6$ TU/ml) compared to the adenoviral system (up to $10^{12}$ TU/ml) means that human cells are infected at a very low efficiency, as described above. Thus, the low titer produced by existing vector systems is highly problematic for stem cell infection and other applications.

B. Lentiviral Vectors

As used herein, the term "lentivirus" refers to a group (or genus) of retroviruses that give rise to slowly developing disease and those gene delivery vectors derived therefrom. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells). In certain non-limiting embodiments, the pseudotyped virus is FIV.

Lentivirus virions have bar-shaped nucleoids and contain genomes that are larger than other retroviruses. Lentiviruses use a tRNA$^{lys}$ as primer for negative-strand synthesis, rather than the tRNA$^{pro}$ commonly used by other infectious mammalian retroviruses. The lentiviral genomes exhibit homology with each other, but not with other retroviruses (See, Davis et al., 1990).

Lentiviruses including HIV, SIV, feline immunodeficiency virus (FIV) and equine infectious anemia virus (EIAV) depend on several viral regulatory genes in addition to the simple structural gag-pol-env genes for efficient intracellular replication. Thus, lentiviruses use more complex strategies than classical retroviruses for gene regulation and viral replication, with the packaging signals apparently spreading across the entire viral genome. These additional genes display a web of regulatory functions during the lentiviral life cycle. For example, upon HIV-1 infection, transcription is up-regulated by the expression of Tat through interaction with an RNA target (TAR) in the LTR. Expression of the full-length and spliced mRNAs is then regulated by the function of Rev which interacts with RNA elements present in the gag region and in the env region (RRE) (Schwartz et al., 1992). Nuclear export of gag-pol and env mRNAs is dependent on the Rev function. In addition to these two essential regulatory genes, a list of accessory genes, including vif, vpr, vpx, vpu, and nef, are also present in the viral genome and their effects on efficient virus production and infectivity have been demonstrated, although they are not absolutely required for virus replication (Wong-Staal, 1991; Subbramanian and Cohen, 1994; and Trono, 1995). In certain embodiments of the invention, pseudotyped viruses are used as gene delivery agents.

C. Jaagsiekte Sheep Retrovirus (JSRV)

The genomic sequence of an infective Jaagsiekte sheep retrovirus (JSRV) has been isolated and characterized, see PCT application WO 01/04266, which is incorporated herein by reference. Normally, sheep have 15 to 20 copies of JSRV-related endogenous retroviruses, some of which are transcriptionally active. Sequence analysis of JSRV has shown that it possesses the hallmarks of integrated retroviral proviruses, such as the presence of a CA-TG dinucleotide pair present at the termini of the upstream and downstream viral LTRs, the loss of 2 nucleotides (nt) from the termini of the LTRs during integration, and an apparent duplication of 6 nt of cellular flanking sequences at the integration site.

A JSRV provirus is about 7,834 bp long, and the viral genome (repeat to repeat) is 7,455 nt. JSRV shows the characteristic genomic organization of type D and type B retroviruses, with pro in a different open reading frame from pol. JSRV typically has a gag protein; a pol protein; a env protein. The JSRV genome comprises Long-Terminal Repeat (LTR) sequences at the 5' and 3' end of the retroviral genome, wherein the LTR is active in pulmonary epithelial cells. The genomic sequence encodes Gag protein, Pol protein, and env protein, and contains cis-acting nucleic acid sequences necessary for reverse transcription, packaging and integration in a target cell. An exemplary JSRV has a genomic sequence as set forth in GenBank accession no. AF105220. The receptor for the JSRV envelope, termed HYAL 2, is widely expressed in human tissues and provides for varied host range of a JSRV pseudotyped vector.

II. Envelope Glycoproteins (env) For Pseudotyping

Typically, retroviruses are enveloped (i.e., surrounded by a host cell-derived lipid bilayer membrane) single-stranded RNA viruses which infect animal cells. Mature viral particles containing two copies of genomic RNA bud from the surface of the infected cell. The viral particle comprises the genomic RNA, reverse transcriptase and other pol gene products inside the viral capsid (which contains the viral gag gene products) which is surrounded by a lipid bilayer membrane derived from the host cell containing the viral envelope glycoproteins (env). The term "envelope glycoproteins" refers to proteins which are associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

Certain embodiments of the invention include various envelope proteins from various viruses. For example, all or part of the JSRV env protein as set forth in SEQ ID NO:3 may be used in various embodiments of the invention. In certain embodiments the size of the env protein may comprise, but is not limited to about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid molecule residues, and any range derivable therein.

As used herein, an "amino acid molecule" refers to any amino acid, amino acid derivative or amino acid mimic as would be known to one of ordinary skill in the art. In certain embodiments, the residues of the env protein are sequential, without any non-amino molecule interrupting the sequence of amino molecule residues. In other embodiments, the sequence may comprise one or more non-amino molecule moieties. In particular embodiments, the sequence of residues of the env protein may be interrupted by one or more non-amino molecule moieties.

A. Env Expression Cassettes

Heterologous env proteins of the invention are typically provided for the pseudotyping of a viral particle. Heterologous env proteins may be introduced into a cell by transfection or transduction of an expression cassette. Generally an expression cassette comprises control sequences and a nucleic acid to be expressed in a manner that expression may be achieved by introduction into a cell. In addition to control sequences for modulation of transcription and translation, vectors and expression vectors may contain nucleic acid sequences that serve other functions as well and are described herein.

An exemplary expression cassette is illustrated in FIG. 1. FIG. 1 illustrates an expression cassette comprising a CMV promoter controlling the transcription a nucleic acid to be expressed. The exemplary nucleic acid sequence is derived form a JSRV, however other similar nucleic acid sequences may be used. Examples of other promoters that may be used are described herein. The nucleic acid to be expressed typically comprises a 5' LTR element, a env protein, and a 3' LTR element. An expression cassette of the invention may include one or more of these elements as well as other nucleic acid elements.

The 5' LTR element may include R and U5 regions of a viral LTR as well as a portion of the gag region. The gag region will, in most instances, include a splice donor site. The gag region may include 5, 10, 15, 20, 25, 30, 35, 40, 45, 50, 55, 60, 65, 100, 200 nucleotides or more of the 5' gag region. In particular embodiments, the splice donor site will be the major splice donor site of JSRV. The env region of the nucleic acid region to be expressed may include a portion of a pol gene that includes a 3' splice acceptor site. The portion of the pol region may include 5, 10, 15, 20, 25, 30, 35, 40, 45, 50, 55, 60, 65 100, 200 nucleotides or more of the 3' pol region. Consensus splice donor and acceptor sites are know (see FIG. 2B, for example), thus one of skill would be capable of using splice sites derived from other viruses or genomes, as well as synthesizing and using nucleic acid fragments encoding such.

An expression cassette of the invention will include all or part of a 3' LTR, in particular the 3' LTR of JSRV. The 3' LTR may include the U3, R and/or U5 regions of a viral LTR.

B. Env Variants

Amino acid sequence variants of the polypeptides of the present invention can be substitutional, insertional or deletion variants. Deletion variants lack one or more residues of the native protein that are not essential or impart a modified function, such as cell, tissue or organ specificity. Insertional mutants typically involve the addition of material at a non-terminal point in the polypeptide. This may include the insertion of an immunoreactive epitope, a targeting peptide or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage or tropism, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine or histidine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "functionally equivalent codon" is used herein to refer to codons that encode the same amino acid, such as the six codons for arginine or serine, and also refers to codons that encode biologically equivalent amino acids (see Table 1, below).

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of a biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, cell surface binding regions. Since it is the interactive capacity and nature of a protein that defines that protein's biological functional activity, certain amino acid substitutions can be made in a protein sequence, and in its underlying DNA coding sequence, and nevertheless produce a protein with like or altered properties. Further, substitutions may be made in a protein to produce a protein with engineered properties, such as cell type specific binding. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

TABLE 1

CODON TABLE

| Amino Acids | | | Codons |
| --- | --- | --- | --- |
| Alanine | Ala | A | GCA GCC GCG GCU |
| Cysteine | Cys | C | UGC UGU |
| Aspartic acid | Asp | D | GAC GAU |
| Glutamic acid | Glu | F | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |

TABLE 1-continued

CODON TABLE

| Amino Acids | | | Codons |
|---|---|---|---|
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred. Similarly, a substitution of amino acid differing in such characteristics may be used to alter to biologic function of the protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the nucleotides of SEQ ID NOS: 1 or 2 will be nucleic acid sequences that are "essentially as set forth in SEQ ID NOS: 1 or 2."

1. Envelope Fusion Proteins

A specialized kind of insertional variant is the fusion protein. In various embodiments of the invention, an envelope protein may be a fusion protein. A fusion protein may be used to provide specific characteristics to a pseudotyped particle, such as tropism, stability or both. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a region to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

2. Targeting Modifications

Envelope glycoproteins of the invention, in particular JSRV env, may be modified by coupling or fusing all or part of the polynucleotide or protein encoded by the polynucleotide to a targeting ligand. The targeting ligand may direct, redirect, target or enhance binding of the pseudotyped virus of the invention to a specific cell, tissue and/or organ.

Pseudotype viruses were originally created to overcome problems encountered by gene therapy vectors' natural host cell tropisms. In recent years, many gene therapy patents have issued wherein the vector contains a heterologous polypeptide used to target the vector to specific cells, such as vectors containing chimeric fusion glycoproteins (Kayman et al., U.S. Pat. No. 5,643,756, incorporated herein by reference) and vectors that contain an antibody to a virus coat protein (Cotten et al., U.S. Pat. No. 5,693,509). The pseudotyped virus of the invention may be genetically modified in such a way that the virus is targeted to a particular cell type (e.g., smooth muscle cells, hepatic cells, renal cells, fibroblasts, keratinocytes, stem cells, mesenchymal stem cells, bone marrow cells, chondrocyte, epithelial cells, intestinal cells, neoplastic cells and others known in the art) such that the nucleic acid genome is delivered to a target non-dividing, a target dividing cell, or a target cell that has a proliferative or other disorder. One way of targeting viruses is to direct the virus to a target cell by preferentially binding to cells having a molecule on the external surface of the cell. This method of targeting the virus utilizes expression or incorporation of a targeting ligand on or into the coat of the virus to assist in targeting the virus to cells or tissues that have a receptor or binding molecule which interacts with the targeting ligand on the surface of the virus. After infection of a cell by the virus, the virus injects its nucleic acid into the cell and the genetic material can be processed and expressed in the host cell. The genetic material may be integrated into the genome of the host cell or episomally maintained within the host cell.

In certain embodiments of the invention, an env may be modified to include a targeting moiety, such that a pseudotyped virus may be delivered to specific cell types or tissues.

Preferably, the targeting ligand is operably linked to the env, creating a chimeric or modified env protein. The addition of targeting ligands impart the ability to pseudotyped virus to bind and deliver nucleic acids to particular cells and/or tissues. The targeting specificity of the ligand-based delivery systems are based on the distribution of the ligand receptors on different cell types. A targeting ligand may either be non-covalently or covalently associated with a env incorporated into a viral envelope.

In certain embodiments, a heterologous nucleic acid sequence of interest may be inserted into the viral vector of the invention. Once the viral vector is associated with a viral particle, the viral particle may be pseudotyped, as described herein, using a targeted heterologous env. For example, a heterologous env may be operatively coupled to a ligand for a receptor on a specific target cell. Heterologous envs can be made target specific by attaching, for example, a sugar, a glycolipid, peptide or a protein. Targeting can be accomplished by using an antibody to target the viral vector. Those of skill in the art will know of, or can readily ascertain, specific polynucleotide sequences which can be inserted into the viral genome or proteins which can be attached to a viral envelope to allow target specific delivery of the viral vector containing the nucleic acid sequence of interest.

Certain embodiments of the invention, includes a chimeric or modified env glycoprotein comprising an env glycoprotein, e.g., a JSRV env glycoprotein, operably linked to a targeting polypeptide. The targeting polypeptide can be a cell specific receptor molecule, a ligand for a cell specific receptor, an antibody or antibody fragment to a cell specific antigenic epitope or any other ligand easily identified in the art which is capable of binding or interacting with a target cell.

Targeting ligands are any ligand specific for a characteristic component of the targeted region. Preferred targeting ligands include proteins such as polyclonal or monoclonal antibodies, antibody fragments, or chimeric antibodies, enzymes, peptides or hormones, or sugars such as mono-, oligo- and polysaccharides. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of resistant cells, to increase transduction of target cells, or to limit transduction of undesired cells, antibody or cyclic peptide targeting moieties (ligands) may be associated with the a pseudotyped virus. The antibody targeting moiety in particular examples is a monoclonal anti-EGF receptor antibody. EGF stimulates cell growth and proliferation through interaction with an EGF receptor. EGF receptors are distributed on the cell surface of various organs and are present in bums, wounds, dermis and tumors. In particular embodiments, the peptide targeting moiety is a cyclic peptide containing within its sequence a RGD integrin binding motif. Ligands such as the RGD peptide that bind to integrins on the cell surface can mediate internalization, thus increasing the efficiency of delivery of the targeted complex. The targeting peptide may include an RGDFV sequence, wherein the peptide includes the RGD sequence in which the peptide is from 3 to 30 amino acids in length. In other embodiments the RGD integrin binding motif is from 3 to 20 amino acids in length or 4 to 10 amino acids in length. In particular embodiments of the present invention, the RGD integrin binding motif is a peptide 5 amino acids in length. Although cyclic peptides which contain the RGD integrin binding motif within its sequence are preferred, linear peptides may also be utilized in the present invention.

Antibodies described by Nicholson et al. (U.S. Pat. No. 5,902,584), which bind the G-CSF extracellular domain can be used in the present invention for targeting pseudotyped viruses. Alternatively, monoclonal antibody fragments may be used to target delivery to specific organs in the animal including brain, heart, lungs or liver. An exemplary method for targeting viral particles to cells that lack a single cell-specific marker is described (U.S. Pat. No. 5,849,718). For example, antibody A may have specificity for tumor, but also for normal heart and lung tissue, while antibody B has specificity for tumor but also normal liver cells. Clearly, the use of antibody A or antibody B alone to deliver an anti-proliferative nucleic acid to the tumor would possibly result in unwanted damage to heart and lung or liver cells. However, antibody A and antibody B can be used together for improved cell targeting. Thus, antibody A is coupled to a gene encoding an anti-proliferative nucleic acid and is delivered, via a receptor mediated uptake system, to tumor as well as heart and lung tissue. However, the gene is not transcribed in these cells as they lack a necessary transcription factor. Antibody B is coupled to a universally active gene encoding the transcription factor necessary for the transcription of the anti-proliferative nucleic acid and is delivered to tumor and liver cells. Therefore, in heart and lung cells only the inactive anti-proliferative nucleic acid is delivered, where it is not transcribed, leading to no adverse effects. In liver cells, the gene encoding the transcription factor is delivered and transcribed, but has no effect because no an anti-proliferative nucleic acid gene is present. In tumor cells, however, both genes are delivered and the transcription factor can activate transcription of the anti-proliferative nucleic acid, leading to tumor-specific toxic effects.

Many other ligands may be employed for the targeting step of pseudotyped virus preparations, depending upon the site targeted for pseudotyped virus delivery. In certain embodiments, it is contemplated that pseudotyped viruses are targeted to specific cell types by receptor-mediated endocytosis. For example, lactosyl ceramide, and peptides that target the LDL receptor related proteins, such as apolipoprotein E3 ("Apo E") have been useful in targeting liposomes to the liver (Spanjer and Scherphof, 1983; WO 98/0748). The asialoglycoprotein, asialofetuin, which contains terminal galactosyl residues, also has been demonstrated to target liposomes to the liver (Spanjer and Scherphof, 1983; Hara et al., 1995). The sugars mannosyl, fucosyl or N-acetyl glucosamine, when coupled to the backbone of a polypeptide, bind the high affinity manose receptor (U.S. Pat. No. 5,432,260, specifically incorporated herein by reference in its entirety). Thus, these glycoproteins can be conjugated to pseudotyped viruses of the present invention and are contemplated as useful for targeting specific cells (e.g., macrophages).

Folate and the folate receptor have also been described as useful for cellular targeting (U.S. Pat. No. 5,871,727). In this example, the vitamin folate is coupled to the JSRV env glycoprotein. The folate receptor has high affinity for its ligand and is overexpressed on the surface of several malignant cell lines, including lung, breast and brain tumors. Transferrin mediated delivery systems target a wide range of replicating cells that express the transferrin receptor (Gilliland et al., 1980).

The addition of targeting ligands for gene delivery for the treatment of hyperproliferative diseases permits the delivery of genes whose gene products are more toxic than do non-targeted systems. Examples of the more toxic genes that can be delivered includes pro-apoptotic genes such as Bax and Bak plus genes derived from viruses and other pathogens such as the adenoviral E4orf4 and the *E. coli* purine nucleoside phosphorylase, a so-called "suicide gene" which converts the prodrug 6-methylpurine deoxyriboside to toxic purine 6-methylpurine. Other examples of suicide genes used with prodrug therapy are the *E. coli* cytosine deaminase gene and the HSV thymidine kinase gene.

The pseudotyped viruses of the invention can be targeted to specific regions of the body by attachment of specific targeting ligands to provide rapid accumulation and concentration of pseudotyped viruses and, correspondingly, of nucleic acid molecules, in a designated tissue. The ligands contemplated for use in the present invention can be conjugated to the pseudotyped viruses by a variety of methods. Various compositions and methods for coupling a targeting ligand to an env protein are known in the art.

III. Nucleic Acids Used in Pseudotyping or Therapy

Nucleic acids of the present include expression vectors and cassettes for both pseudotyping and therapeutic genes. Certain embodiments of the present invention include the nucleic acids of SEQ ID NOS:1 or 2. In certain embodiments, wild-type and/or mutant versions of these sequences are employed. In particular aspects, a nucleic acid encodes for or comprises a transcribed nucleic acid. In other aspects, a nucleic acid comprises a nucleic acid segment of SEQ ID NOS: 1 or 2, or a biologically functional equivalent thereof.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 8 and about 100 nucleobases in length. The term "polynucleotide" refers to at least one molecule of greater than about 100 nucleobases in length.

Herein certain embodiments, a "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide, such as all or part of a JSRV env glycoprotein. As will be understood by those in the art, this functional term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

A polynucleotide of the invention may form an "expression cassette." An "expression cassette" is polynucleotide that provides for the expression of a particular transcription unit. That is it includes promoter elements and various other elements that function in the transcription of a gene or transcription unit, such as a polynucleotide encoding all or part of a env protein, in particular JSRV env protein. Other elements may include one or more titer enhancing elements of the invention. An expression cassette may also be part of a larger replicating polynucleotide or expression vector or construct.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

"Isolated substantially away from other coding sequences" means that the gene of interest forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

As used herein, a "nucleotide" refers to a nucleoside further comprising a "backbone moiety." A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A. Expression Constructs

Expression constructs of the invention may include nucleic acids encoding a protein for use in pseudotyping a particle. In other aspects, the expression construct may be a therapeutic expression construct that can be packaged in a pseudotyped viral particle of the invention for use in therapeutic compositions and methods. In certain embodiments, genetic material may be manipulated to produce expression cassettes and/or expression constructs that encode env proteins, JSRV env proteins or therapeutic genes. Such methods involve the generation of expression constructs or cassettes containing, for example, a DNA encoding a gene of interest and a means for its expression, replicating viral vector in an appropriate helper cell that contains a heterologous env glycoprotein, obtaining viral particles produced therefrom, and infecting cells with the pseudotyped virus particles. In certain embodiments, an expression cassette and/or expression vector may be used to co-express a heterologous env gene for the production of a therapeutic viral composition. The therapeutic viral composition will typically comprises a therapeutic expression construct packaged in a pseudotyped viral particle that is designed for the treatment of and/or vaccination against a particular disease or condition.

Embodiments of the invention may include two separate types of expression cassette or expression construct comprising an expression cassette. One cassette is used in expression of a env protein for psuedotyping. Another expression cassette may encode a therapeutic gene. In the context of a pseudotyping vector, a gene of interest may be a heterologous env gene such as a JSRV env gene. In the context of a therapeutic vector, a therapeutic gene may be a therapeutic gene discussed herein useful in the prophylatic or therapeutic treatment of a disease condition. In the context of gene therapy, the gene may be a heterologous DNA, meant to include DNA derived from a source other than the viral genome which provides the backbone of the vector. Finally, the virus may act as a live viral vaccine and express an antigen of interest for the production of antibodies thereagainst. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA also may include a regulatory sequence which may be derived from one source and the gene from a different source.

In order to mediate the expression of a pseudotyping protein or a therapeutic gene in a cell, it will be necessary to transfer the pseudotyping or therapeutic expression constructs of the present invention into a cell. Such transfer may employ viral or non-viral methods of gene transfer.

Gene transfer may be accomplished using a variety of techniques known in the art, including but not limited to adenovirus, various retroviruses, adeno-associated virus, vaccinia virus, canary pox virus, herpes viruses.

Various methods and compositions for nucleic acid transfer, both ex vivo and in vivo may be found in the following references: Carter and Flotte, 1996 ; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996; Xiao et al., 1996; McCown et al., 1996; Ping et al., 1996; Ridgeway, 1988; Baichwal and Sugden, 1986; Coupar et al., 1988.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), naked DNA expression construct (Klein et al., 1987; Yang et al., 1990), Liposomes (Ghosh and Bachhawat, 1991; Radler et al., 1997; Nicolau et al. 1987; Kaneda et al., 1989; Kato et al., 1991) and receptor-mediated transfection (Wu and Wu, 1987; Wu and Wu, 1988).

Once the construct has been delivered into the cell the nucleic acid encoding the pseudotyping or therapeutic gene may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

1. Control Regions

Expression cassettes and/or constructs of the invention, whether they encode a heterologous env gene or a therapeutic gene will typically include various control regions. These control region typically modulate the expression of the gene of interest.

a. Promoters

Throughout this application, the term "expression construct" is meant to include any type of genetic construct containing a nucleic acid coding for gene products in which part or all of the nucleic acid encoding sequence is capable of being transcribed, e.g., all or part of an env protein or therapeutic protein. The transcript may be translated into a protein, but it need not be. In certain embodiments, expression includes both transcription of a gene and translation of mRNA into a gene product. In other embodiments, expression only includes transcription of the nucleic acid encoding therapeutic genes.

The nucleic acid encoding a gene product is under transcriptional control of a promoter. A "promoter" refers to a DNA sequence recognized by the machinery of the cell, or introduced machinery, required to initiate the specific transcription of a gene. In particular aspects, transcription may be constitutive, inducible, and/or repressible. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for various retroviral promoters, the HSV thymidine kinase (tk) and SV40 early transcription units.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus immediate early gene promoter(CMVIE), the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral, retroviral or mammalian cellular or bacterial phage promoters, which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline.

In some circumstances, it may be desirable to regulate expression of a transgene in a therapeutic expression vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 3).

In certain indications, it may be desirable to activate transcription at specific times after administration of the gene therapy vector. This may be done with such promoters as those that are hormone or cytokine regulatable. For example in therapeutic applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1990), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

Tumor specific promoters such as osteocalcin, hypoxia-responsive element (HRE), MAGE-4, CEA, alpha-fetoprotein, GRP78/BiP and tyrosinase may also be used to regulate gene expression in tumor cells.

It is envisioned that any of the above promoters alone or in combination with another may be useful according to the present invention depending on the action desired. In addition, this list of promoters should not be construed to be exhaustive or limiting, those of skill in the art will know of other promoters that may be used in conjunction with the promoters and methods disclosed herein.

TABLE 3

TISSUE SPECIFIC PROMOTERS

| Tissue | Promoter |
| --- | --- |
| Pancreas | Insulin |
| | Elastin |
| | Amylase |
| | pdr-1 pdx-1 |
| | glucokinase |
| Liver | Albumin PEPCK |
| | HBV enhancer |
| | α fetoprotein |
| | apolipoprotein C |
| | α-1 antitrypsin |
| | vitellogenin, NF-AB |
| | Transthyretin |
| Skeletal muscle | Myosin H chain |
| | Muscle creatine kinase |
| | Dystrophin |
| | Calpain p94 |
| | Skeletal alpha-actin |
| | fast troponin 1 |
| Skin | Keratin K6 |
| | Keratin K1 |
| Lung | CFTR |
| | Human cytokeratin 18 (K18) |
| | Pulmonary surfactant proteins A, B and C |
| | CC-10 |
| | P1 |
| Smooth muscle | sm22 α |
| | SM-alpha-actin |
| Endothelium | Endothelin-1 |
| | E-selectin |
| | von Willebrand factor |
| | TIE (Korhonen et al., 1995) |
| | KDR/flk-1 |
| Melanocytes | Tyrosinase |
| Adipose tissue | Lipoprotein lipase (Zechner et al., 1988) |
| | Adipsin (Spiegelman et al., 1989) |
| | acetyl-CoA carboxylase (Pape and Kim, 1989) |
| | glycerophosphate dehydrogenase (Dani et al., 1989) |
| | adipocyte P2 (Hunt et al., 1986) |
| Blood | β-globin | b. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 4 and Table 5). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

In preferred embodiments of the invention, a therapeutic expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

TABLE 4

| ENHANCER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |

TABLE 4-continued

| ENHANCER |
|---|
| Human Immunodeficiency Virus |
| Cytomegalovirus |
| Gibbon Ape Leukemia Virus |

TABLE 5

| Element | Inducer |
|---|---|
| MT II | Phorbol Ester (TPA) |
| | Heavy metals |
| MMTV (mouse mammary tumor virus) | Glucocorticoids |
| β-Interferon | Poly(rI)X |
| | Poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose | c. Polyadenylation Signals

Polyadenylation signals may be used in both pseudotyping and therapeutic expression vectors. Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

2. Therapeutic Genes

Pseudotyped viral particles of the invention may be used to deliver a variety of therapeutic agents, including therapeutic expression vectors. The present invention contemplates the use of a variety of different therapeutic genes. For example, genes encoding enzymes, hormones, cytokines, oncogenes, receptors, ion channels, tumor suppressors, transcription factors, drug selectable markers, toxins and various antigens are contemplated as suitable genes for use according to the present invention. In addition, antisense constructs derived from oncogenes are other "genes" of interest according to the present invention.

In accordance with the present invention, a selected gene or polypeptide may refer to any protein, polypeptide, or peptide. A therapeutic gene or polypeptide is a gene or polypeptide which can be administered to a subject for the purpose of treating or preventing a disease. For example, a therapeutic gene can be a gene administered to a subject for treatment or prevention of cancer. Examples of therapeutic genes include, but are not limited to, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, Bax, Bak, Bik, Bim, Bid, Bad, Harakiri, Fas-L, mda-7, fus, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, -glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, -L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

In yet another embodiment, the heterologous gene may include a single-chain antibody. Methods for the production of single-chain antibodies are well known to those of skill in the art. The skilled artisan is referred to U.S. Pat. No. 5,359, 046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules can be used in combination with the present invention, including antibodies against oncogenes, toxins, hormones, enzymes, viral or bacterial antigens, transcription factors, receptors and the like.

3. Multigene Constructs and IRES

In certain embodiments of the invention, the use of internal ribosome binding sites (IRES) elements are used to create multigene polycistronic messages. IRES elements are able to bypass the ribosome scanning model of 5'-methylated, Cap-dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

4. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266 032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959, 463, 5,428,148, 5,554,744, 5,574,146, 5,602,244, each of which are incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

5. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

6. Nucleic Acid Segments

In certain embodiments, the nucleic acid is a nucleic acid segment. As used herein, the term "nucleic acid segment," are smaller fragments of a nucleic acid, such as for non-limiting example, those that encode only part of the SEQ ID NOS: 1 or 2. Thus, a "nucleic acid segment" may comprise any part of a gene sequence, of from about 8 nucleotides to the full length of the SEQ ID NOS: 1 or 2.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. This algorithm would be applied to each of SEQ ID NOS: 1 or 2. As used herein, a "probe" generally refers to a nucleic acid used in a detection method or composition. As used herein, a "primer" generally refers to a nucleic acid used in an extension or amplification method or composition.

In a non-limiting example, one or more nucleic acid constructs may be prepared that include a contiguous stretch of nucleotides identical to or complementary to SEQ ID NOS: 1 or 2. A nucleic acid construct may be about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 60, about 70, about 80, about 90, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 14, about 15, about 16, about 17, about 18, about 19, about, 20, about 21, about 22, about 23, about 24, about 25, about 26, about 27, about 28, about 29, about 30, about 35, about 40, about 50, about 60, about 70, about 80, about 90, about 100, about 125, about 150, about 175, about 200, about 500, about 1,000, about 10,000, about 50,000, about 100,000, about 250,00, about 500,00, about 1,000,000 or more bases.

The present invention also encompasses a nucleic acid that is complementary to SEQ ID NOS: 1 or 2. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule of SEQ ID NOS: 1 or 2 during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

IV. Pharmaceutical Compositions and Routes of Administration

Where clinical applications are contemplated, it will be necessary to prepare pharmaceutical compositions of the pseudotyped viral compositions (therapeutic compositions) in a form appropriate for the intended application. Generally, this will entail preparing compositions that are essentially free of pyrogens, as well as other impurities that could be harmful to humans or animals.

One will generally desire to employ appropriate salts and buffers to render the compositions suitable for introduction into a patient. Aqueous compositions of the present invention comprise an effective amount of the therapeutic agent dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients, such as other anti-viral agents, can also be incorporated into the compositions.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

An effective amount of the composition is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

Also contemplated are combination compositions that contain two active ingredients. In particular, the present invention provides for compositions that contain pseudotyped vector compositions and at least a second therapeutic, for example, an anti-neoplastic drug.

A. Parenteral Administration

The active compositions of the present invention may be formulated for parenteral administration, e.g., formulated for injection via the intravenous, intramuscular, sub-cutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active agents may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the particular methods of preparation are vacuum-drying and freeze-drying techniques which yield a powder of the active ingredient plus any additional desired ingredient from a previously sterile-filtered solution thereof.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Vector production. All of the viral vectors used in this study were approved for use at biosafety level 2 by the University of Iowa Health Protection Office. The second-generation FIV vector system utilized in this study was reported previously (Wang et al., 1999; Johnston et al., 1999). The FIV vector construct expressed the β-galactosidase cDNA directed by the CMV promoter. The envelope constructs in this study utilized the CMV early gene promoter to direct transcription. Envelopes used include the Jaagsiekte sheep retrovirus (JSRV) (Palmarini et al., 2000), the vesicular stomatitis virus G protein (VSV-G), Enzootic nasal tumor virus (OENTV) (Cousens et al., 1999), and the Marburg (Musoke variant) envelope GP (pMBGP (Sinn et al., 2003). The Ebola envelope GP with an internal deletion EBOΔO (pEZGP 309-489) has been previously described (Sinn et al., 2003; Jeffers et al., 2002). Pseudotyped FIV vector particles were generated by transient transfection of plasmid DNA into 293T cells as described previously (Johnston et al., 1999). FIV vector titers described in this study were following 250-fold centrifugation concentration and all preparations were titered on HT1080 cells at limiting dilutions.

Plasmid expression vectors. The JSRV env expression construct termed pCMV3JS21ΔGP was constructed as previously described (Maeda et al., 2001). The constructs J, 5'J, J3', and 5'J3' were constructed by PCR amplification followed by ligation into pcDNA3.1/V5-His TOPO (Cat. No. #45-0005; Invitrogen, Carlsbad, Calif.) using the manufacturer's protocol. The following primers were used for the amplification: (1) 5'-gcagagtatcagccatttt-3' SEQ ID NO:4; (2) 5'-tattaatatggggacgaggg-3' SEQ ID NO:5; (3) 5'-gggtggcggga-cagggag-3' SEQ ID NO:6; and (4) 5'-gtaatacgactcactataggc-3' SEQ ID NO:7 (T7 Primer). Construct J was amplified with primers 2 and 3; 5'J was amplified with 1 and 3; J3' was amplified with 2 and 4; and 5'J3' was amplified with 1 and 4. This same strategy was used to construct plasmids for stable transfection into TREX cells (described below) with the exception that the cloning vector was pcDNA5/FRT/V5-HIS (Cat. No. #450093; Invitrogen, Carlsbad, Calif.). Mutating the splice donor in pCMV3JS21ΔGP to construct pCMV3JS21ΔGPΔSD was achieved with the QuikChange Site Directed Mutagenesis Kit (Cat. No. #200518, Stratagene, La Jolla, Calif.) using the manufacturer's protocol and the following mutagenesis primers: 5'ctcattaattgaaacgatcgag-tatatgg-3' SEQ ID NO:8 and 5'-ccatatactcgatcgtttcaattaatgag-3' SEQ ID NO:9. The pIXSL expression plasmid was constructed in a two-stage process. First, the deletion of JSRV env orf was achieved by amplification of the pCMV3JS21ΔGP template with the following primers: upstream 5'-cccaatacgcaaaccgcctctcccc-3' SEQ ID NO:10 (this primer anneals to a region within pBluescript) and downstream 5'-ggtacttgtc ctaggctttg gcttctgcca aagagctccc aggaattcac ccttctgtgg aaaaacacaa acatgccc-3' SEQ ID NO:11 (this primer deletes the orf and creates a unique EcoRI cloning site.) Second, this amplification product was digested with Avr II and Not I and ligated into an Avr II/Not I digested pCMV3JS21ΔGP plasmid. The pcDNA3.1 based expression plasmids expressing VSV-G, EboΔO, and Marburg have been previously described (Sinn et al., 2003), and each are flanked by EcoRI restriction sites allowing for straightforward cloning into the pIXSL expression plasmid. oENTV was cloned into pCR2.1 TOPO (Invitrogen, Carlsbad, Calif.) and pcDNA3.1/V5-His TOPO following PCR amplification using the primers: 5'-atgccgaag caccgcgct gg-3' SEQ ID NO:12 and 5'-ttaaccctcc acgggttgtc cccc-3' SEQ ID NO:13. oENTV was then moved into pIXSL by using the flanking EcoRI sites contained within the pCR2.1 vector. Construction of pCMV3dGP(HA) was previously described (Maeda et al., 2003). J-HA was constructed by PCR amplification with the primers numbered 2 and 3 from above and ligated into pcDNA3.1/V5-His TOPO. All constructs were confirmed to be free of unintentional PCR introduced mutations by sequencing.

Stable Cell Line Generation and RNA Half-Life Determination. T-Rex® cells (Invitrogen, Carlsbad, Calif.) were maintained in DMEM (Invitrogen, Carlsbad, Calif.) supplemented with 10% fetal bovine serum (Invitrogen, Carlsbad, Calif.), sodium pyruvate and non-essential amino acids as described by the manufacturer's protocol. For mRNA decay studies, cells were grown to 95% confluence and treated with doxycycline (2-200 μg/ml) for 24 hours before the transcription inhibitor actinomycin D (10.0 μg/ml) was added. RNA purification was conducted using TriReagent (MRC, Cincinnati, Ohio) and the manufacturers' protocol. JSRV RNA quantification at progressing timepoints was determined by real-time PCR (described below). Half-life calculations assume completely stochastic mRNA decay and were determined using the formula $C/C_0 = e^{-kdt}$, as previously described (Ross, 1995).

5'RACE. Plasmids were transiently transfected into 293T cells and RNA was purified 24 hours later. A SMART RACE cDNA Amplification Kit (Clontech, Palo Alto, Calif., Cat. No. #634914) and the manufacturer's protocol were utilized to determine the splice junctions as well as the transcriptional start site. The gene specific primer for the reaction was 5'-ggcgcttcgg cattctgtg g-3' SEQ ID NO: 14.

Nuclear/Cytoplasmic Extracts. Nuclear extracts from transiently transfected 293T cells were prepared as previously described (Lee et al., 1988) with the following modifications. Cells from 80% confluent monolayer cultures were harvested and washed in 1× phosphate-buffered saline. Pelleted cells were resuspended in buffer containing 10 mM HEPES, pH 7.9, 1.5 mM MgCl$_2$, 10 mM KCl, and 0.5 mM dithiothreitol, maintained on ice to swell, and lysed by being rapidly and repeatedly drawn through a 26-gauge needle. Following centrifugation, the nuclear and cytoplasmic extracts were separated, the nuclear pellet was washed with 1×PBS and RNA was purified using TriReagent (MRC) and the manufacturer's protocol. JSRV RNA quantification was determined by Dot Blot Assay and normalized to human GAPDH.

Dot Blot Assay. DNA and RNA dot blot hybridization were performed using standard methods. The JSRV cRNA antisense probe was labeled using an in vitro transcription reaction containing (α-$^{32}$P)-UTP and purified using a Sephadex G-50 quick spin column (Boehringer Mannheim, Mannheim, Germany). Quantitations of dot blots were performed using a Molecular Dynamics Storm Phosphorimaging system and ImageQuant software.

Real-Time PCR. Real-Time PCR using the TaqMan universal PCR master mix (Applied Biosystems, Foster City, Calif., Cat. No. #4304437) was utilized to quantify stable cell line JSRV RNA and DNA. The upstream primer: 5'-ccaccca-gag gcaaattga a-3' SEQ ID NO:15; downstream primer: 5'ggt-gtcaccg gaggttgtac a SEQ ID NO:16 ; Probe: 5'-FAM-cgctaatgcg ctacgcctgg aatg-TAMRA-3' SEQ ID NO:17. Levels were normalized to GAPDH using the manufacturer's primers and probe (Applied Biosystems, Foster City, Calif., Cat. No. #402869).

Western Blot Analysis. Western blot analysis for JSRV env GP was conducted using HA-tagged constructs and standard techniques (Maeda et al., 2003). Briefly, cell lysates were denatured for 5 minutes at 100° C. in Laemmli sample buffer, electrophoresed on 10% polyacrylamide gels (BioRad, Hercules, Calif., Cat. No. #161-1155, BioRad) at 125 V, and transferred to pure nitrocellulose (BioRad, Hercules, Calif., Cat. No. #162-0145) overnight at 200 mA. Membranes were probed with a monoclonal anti-HA primary antibody (Roche, Indianapolis, Ind., Cat. No. #1583816), a monoclonal anti-human β-actin (Sigma, St. Louis, Mo., Cat. No. #A-5441), or a mouse IgG2b,κ (Sigma, St. Louis, Mo., Cat. No. #M-8894) isotype control at 1:1000, and detected using goat anti-mouse IgG conjugated to alkaline phosphatase, at 1:1000 dilution (Sigma, St. Louis, Mo., #A-1682).

Example 2

Pseudotyping FIV

Figure 1B:
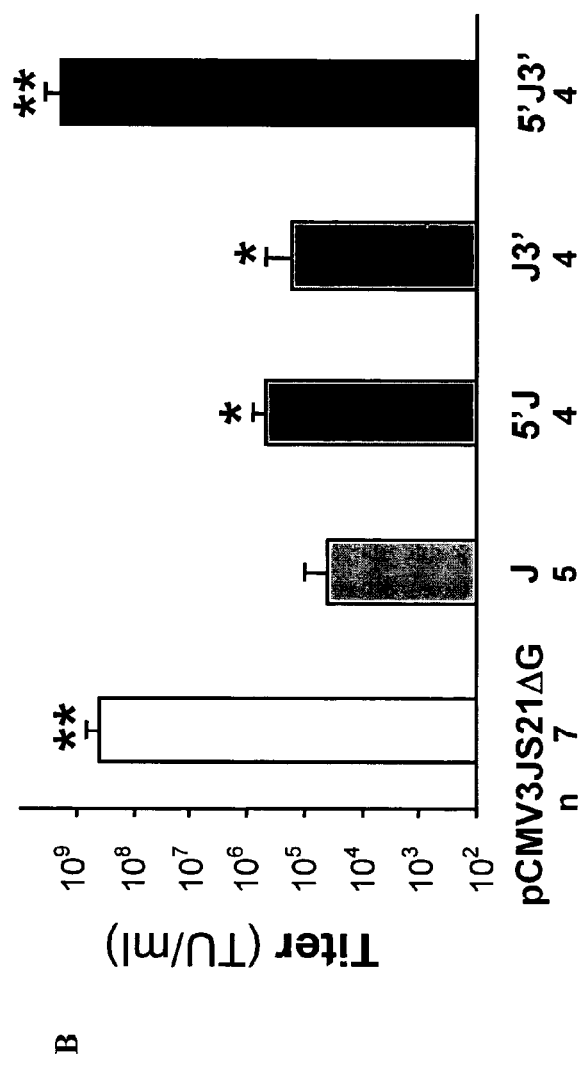

One embodiment of the invention includes the targeting of FIV to airway cells. Studies were carried out to investigate the pseudotyping of FIV with the envelope glycoprotein from the Jaagsiekte Sheep Retrovirus. To study a potentially unique cellular tropism conferred to a lentivirus, the inventors pseudotyped a FIV-based vector (Johnston et al., 1999) with the envelope glycoprotein from the Jaagsiekte sheep retrovirus. The JSRV env GP is a candidate for FIV pseudotyping because of the precedence for retroviral envelopes efficiently pseudotyping other retroviruses as well as the previously reported success with MLV (Rai et al., 2000). A JSRV env expression vector termed "pCMV3JS21ΔGP" was initially cloned by a Pac1/BamH1 proviral deletion as previously described (Maeda et al., 2001). When this clone was introduced into our vector production system we obtained outstanding vector titers of $4 \times 10^8$ TU/ml (FIG. 1B). Concurrently, the JSRV env coding sequence alone was cloned into a standard mammalian expression vector, pcDNA3.1 (Invitrogen, Carlsbad, Calif.), and termed "J". Surprisingly, incorporation of J into three plasmid transfection protocols generated FIV vector titers of only $4 \times 10^4$ TU/ml (FIG. 1B). To discern which regions were contributing to this difference in titer, additional constructs were produced. The construct 5'J contained the JRSV env coding region plus the 5' untranslated region that is present in pCMV3JS21ΔGP (Maeda et al., 2001). This includes R and U5 of the JSRV 5'LTR, as well as partial initial gag sequence and partial terminal pol sequence. When this envelope construct was used to pseudotype FIV, average titers of $4.6 \times 10^5$ TU/ml resulted (FIG. 1B). The construct J3' includes the JSRV env coding sequence as well as the complete 3'LTR and generated average pseudotyped FIV vector titers of $1.5 \times 10^5$ TU/ml (FIG. 1B). Of note, the CMV promoter inserted into the pBluescript backbone for the pCMV3JS21ΔGP was identical in sequence to the CMV promoter of pcDNA3.1. However, to ensure the differences in FIV titer were not an artifact of the plasmid carrying the envelope gene, a fourth plasmid was generated termed 5'J3', in which all of the JSRV derived sequence from pCMV3JS21ΔGP was moved to the pcDNA3.1 plasmid. This envelope construct resulted in average pseudotyped FIV vector titers of $1.9 \times 10^9$ TU/ml (FIG. 1B), suggesting the env expression plasmid backbone is not a contributing factor.

The FIV pseudotyping efficiency by the JSRV envelope GP expressed from a standard mammalian expression plasmid is trivial in comparison to an expression plasmid containing the native proviral flanking sequences. Unexpectedly, these additive increases in vector titer failed to account for the ~10,000-fold increase conferred by inclusion of both the 3' and 5' elements. The results indicate that 5' and 3' proviral sequences act synergistically to increase vector titer.

Figures 2A, 2B:
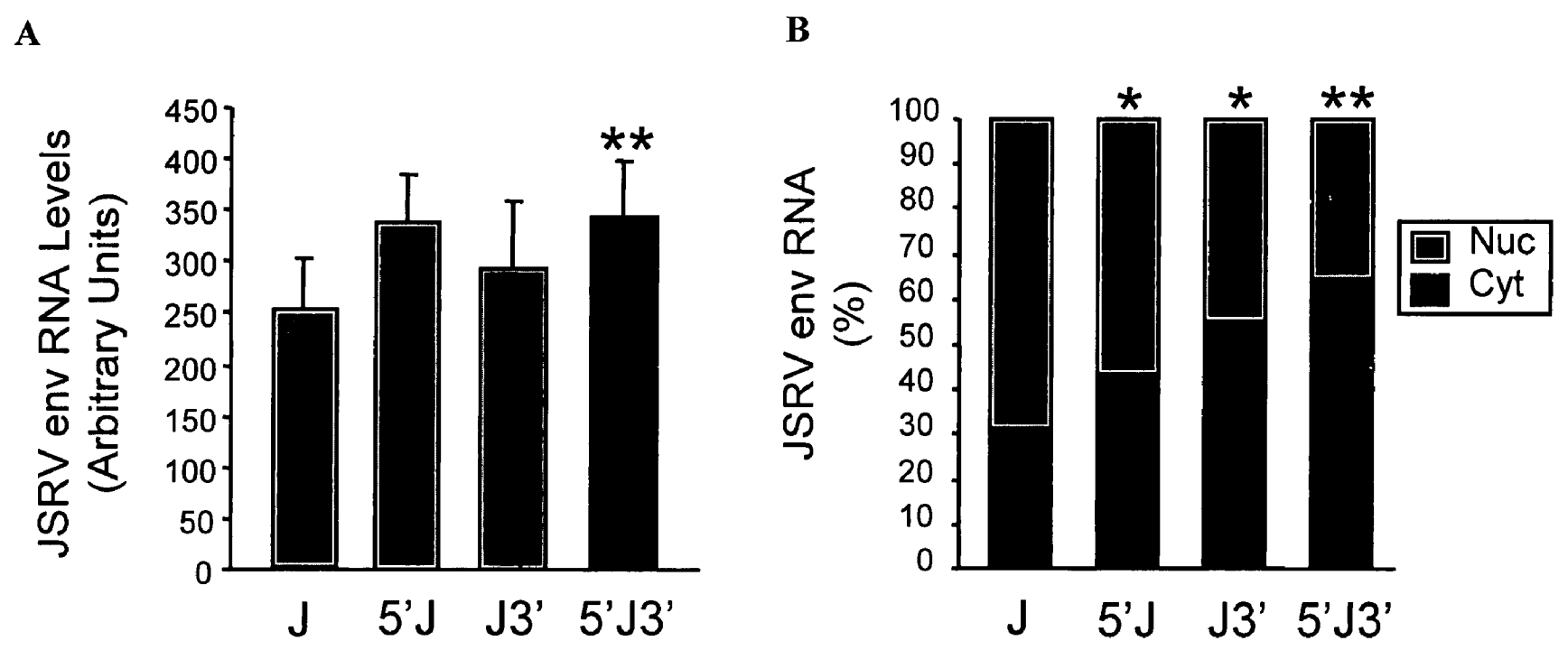

The flanking regions of envelope coding region increased the JSRV env steady state RNA levels and vector titer. Total JSRV env mRNA was determined 24 hours following transient transfection of 5'J3', 5'J, J3', and J using a dot blot assay and quantified by phosphorimaging. Significantly greater levels of JSRV envelope RNA derived from the 5'J3' expression construct were observed compared to the J construct (FIG. 2A). However, the differences between the JSRV env RNA derived from 5'J3' and 5'J or J3' were minimal (FIG. 2A). Interestingly, a clearer distinction emerged when the RNA was purified from cellular extracts that were first separated into nuclear and cytoplasmic fractions. Approximately, 70% of the JSRV env RNA derived from the J construct was within the nuclear fraction, whereas, ~70% of the JSRV env RNA derived from the 5'J3' construct was extranuclear. Approximately 45% and 55% of the 5'J and J3' derived JSRV env RNA, respectively, were extranuclear (FIG. 2B). These data show that elements contained within the JSRV env flanking regions are important for RNA trafficking out of the nucleus. The possibility of promoter enhancing elements in the JSRV R or U5 region of the 5'LTR was addressed by promoter-luciferase analysis (data not shown). A CMV promoter followed by the JSRV 5' region of pCMV3JS21ΔGP was used to drive a luciferase reporter gene. This construct did not result in increased luciferase activity in 293 cells as compared to CMV-luciferase.

Figures 3A, 3B, 3C, 3D:
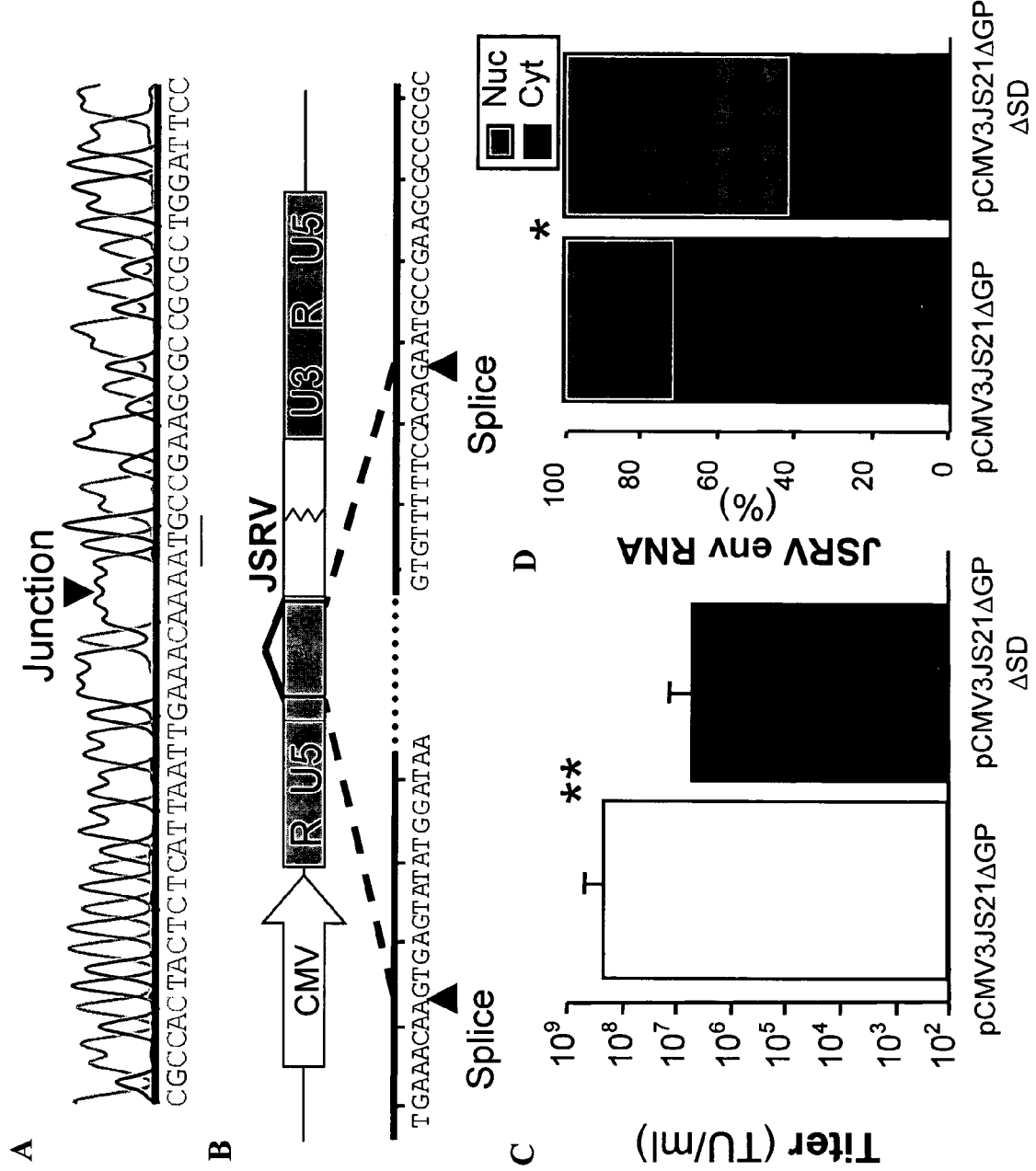

The pCMVJS21ΔGP plasmid contains the major splice donor and the envelope splice acceptor that have been described in the JSRV proviral sequence (Maeda et al., 2001; Palmarini et al., 2002). To confirm the splice event in this expression plasmid, 5'RACE was performed. FIG. 3A displays an excerpt from the resulting RACE sequence confirming that a splice event occurs and the splice junction is indicated. FIG. 3B schematically shows the location of the major splice donor site and the splice acceptor site that occurs two bases upstream from the env start codon. The observed splice junction is identical to the one previously documented from the proviral sequence (Palmarini et al., 2002). To test the contribution of a splice event to the pseudotyped FIV vector titer, the splice donor was removed by site directed mutagenesis. The resulting construct, termed pCMV3JS21ΔGP ΔSD, resulted in a 100-fold decrease in titer from the levels of pCMV3JS21ΔGP (FIG. 3C). The total JSRV env RNA derived 24 hours following transient transfection from either construct was nearly equivalent (data not shown). However, the majority of the JSRV env RNA derived from the pCMV3JS21ΔGP ΔSD construct was localized in the nucleus; whereas, the majority of the JSRV env RNA derived from the pCMV3JS21ΔGP construct was extranuclear (FIG.

3D). These data suggest that the lower titer of FIV pseudotyped with pCMV3JS21ΔGP ΔSD results from less env mRNA available for translation in the cytoplasm. The inclusion of an intron in an expression plasmid will often enhance mRNA translocation from the nucleus (Izaurralde, 2002). Indeed, mutating the splice donor resulted in a significant drop in vector titers (FIG. 3C), suggesting that a splice event contributes to the enhanced vector titer. However, deleting the entire 5' region resulted in a 1,000-fold drop in pseudotyped vector titer (FIG. 1), although this region did not contribute to the transcriptional activity (data not shown).

Figures 4A, 4B:
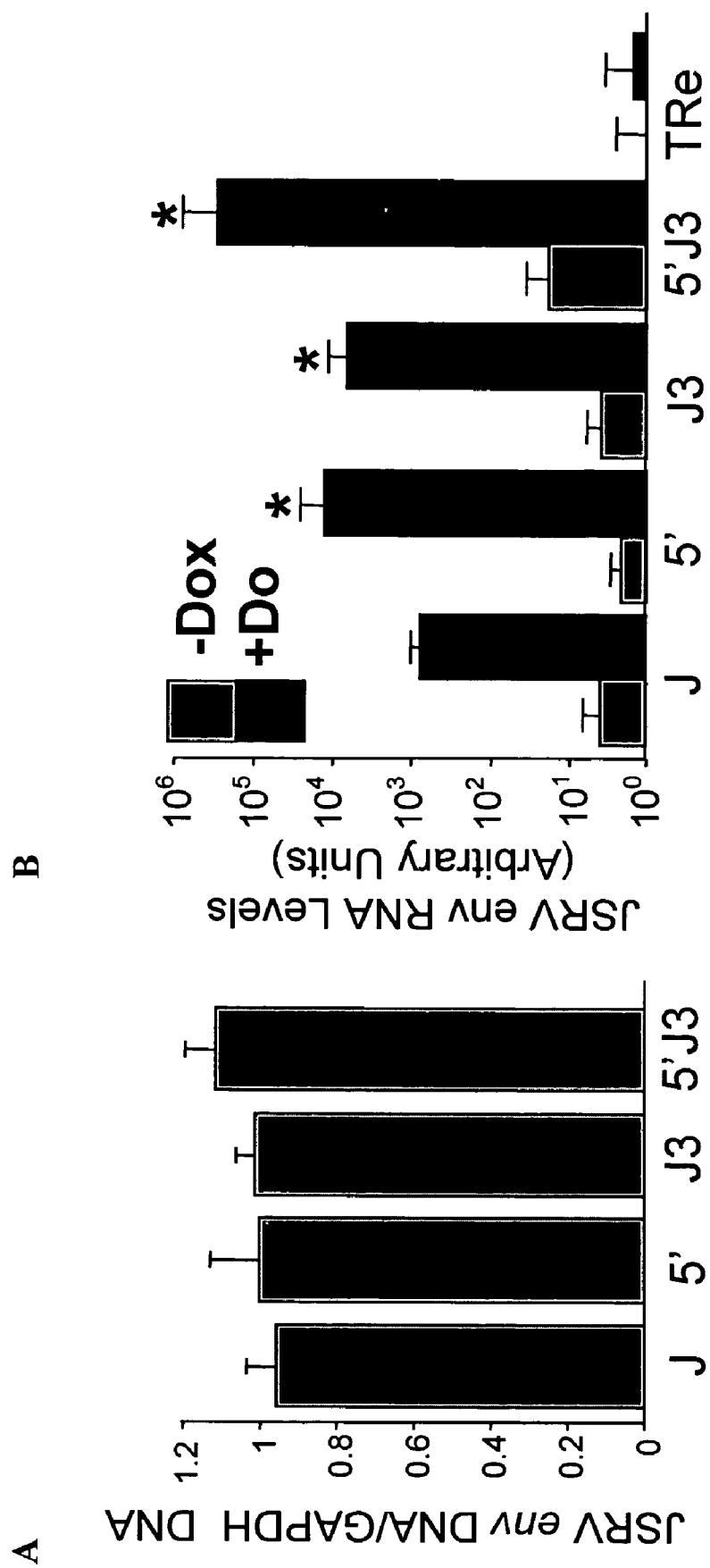

To investigate the accumulation and stability of envelope RNA, stable cell lines expressing the different constructs were generated. Cell lines expressing the J, J3', 5'J, and 5'J3' constructs were generated using a Flp-In stable cell line production system (Invitrogen, Carlsbad, Calif.) with the JSRV env under the control of a Tet-On inducible promoter. This system allows for single copy insertion at a specific genomic locus, thus avoiding expression variability resulting from copy number and position effects. As shown in FIG. 4A, the env copy number from the cell lines are not significantly different as determined by real-time PCR and normalized to human GAPDH. Furthermore, a stable insertion into the appropriate locus in this cell line disrupts a LacZ gene. Unlike the parental cell line, none of the stable cell lines stained blue in the presence of X-gal (data not shown). JSRV env RNA production was further found to be doxycycline regulated (FIG. 4B) in a dose-dependent fashion (data not shown). Following 24 hours doxycycline stimulation, the steady state mRNA levels of 5'J3', 5'J, and J3' were significantly higher than the mRNA levels derived from the J construct, further suggesting that increased vector titers could be attributed, in part, to increased envelope mRNA levels. The effects of the proviral elements on the steady state levels of JSRV env RNA in the stable cells lines was much more pronounced than in the transiently transfected constructs (FIG. 2A). This difference may be due in part to transient transfection efficiency.

Figure 5:
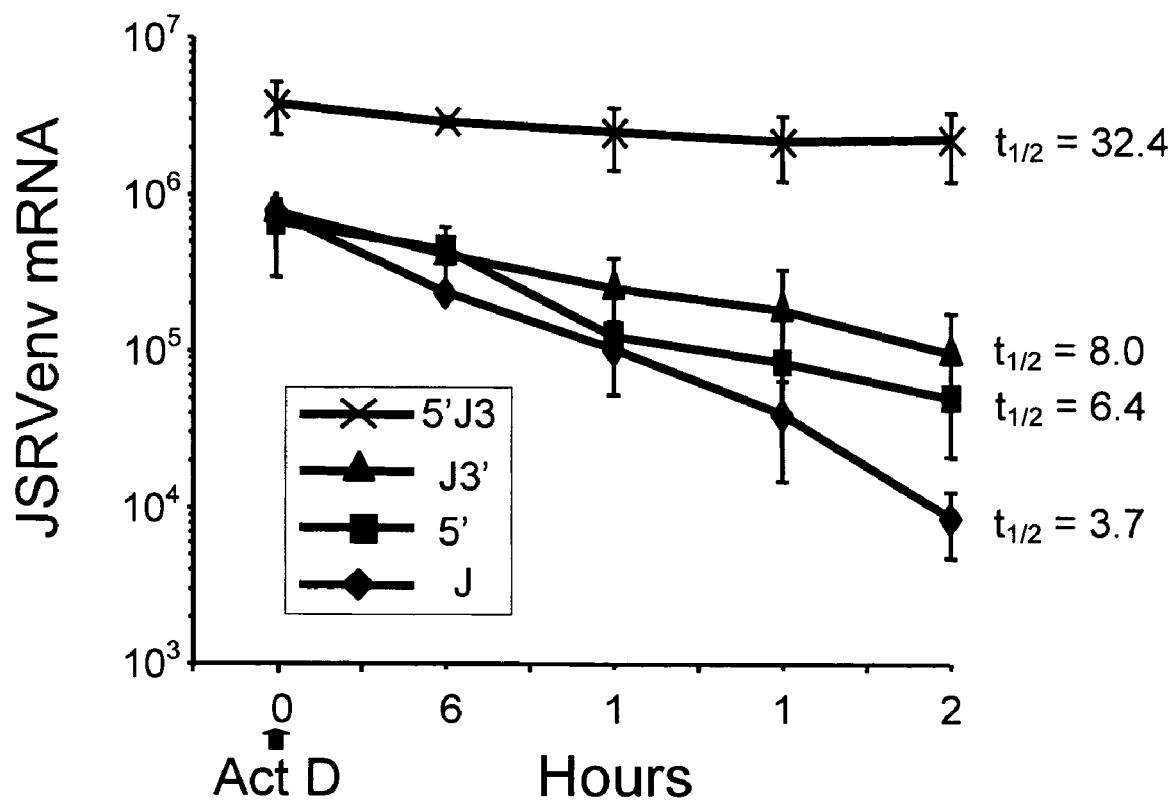

To measure the RNA stability of the various JSRV env constructs, cells were stimulated with doxycycline for 24 hours. Following doxycycline stimulation, the potent transcriptional inhibitor actinomycin D was applied and total RNA was collected at the indicated timepoints (FIG. 5). The 5'J, J3', and 5'J3' cell lines were stimulated with 2 μg/ml doxycycline; however to equilibrate the initial levels of RNA, the J cell line was stimulated with 200 μg/ml doxycycline. RNA levels at each timepoint were determined by real-time PCR (FIG. 5). Interestingly, the JSRV env mRNA half-lives ($t_{1/2}$) in the J, 5'J, J3', and 5'J3' cell lines were found to be 3.7, 6.4, 8.0, and 32.4 hours, respectively. The stability of the JSRV env RNA derived from each construct was consistent with the relative cytoplasmic steady state levels of RNA (FIG. 4B). The presence of the 3' region extended the JSRV env RNA half-life by approximately 2.1-fold and the presence of the 5' region increased the half-life by 1.7-fold. The presence of the 5' and 3' regions significantly extended the JSRV env half-life by greater than 8-fold (FIG. 5). Clearly, the mechanisms underlying the enhanced FIV titer are the result of combined effects, including RNA splicing, nuclear translocation, and increased RNA stability.

Figures 6A, 6B, 6C:
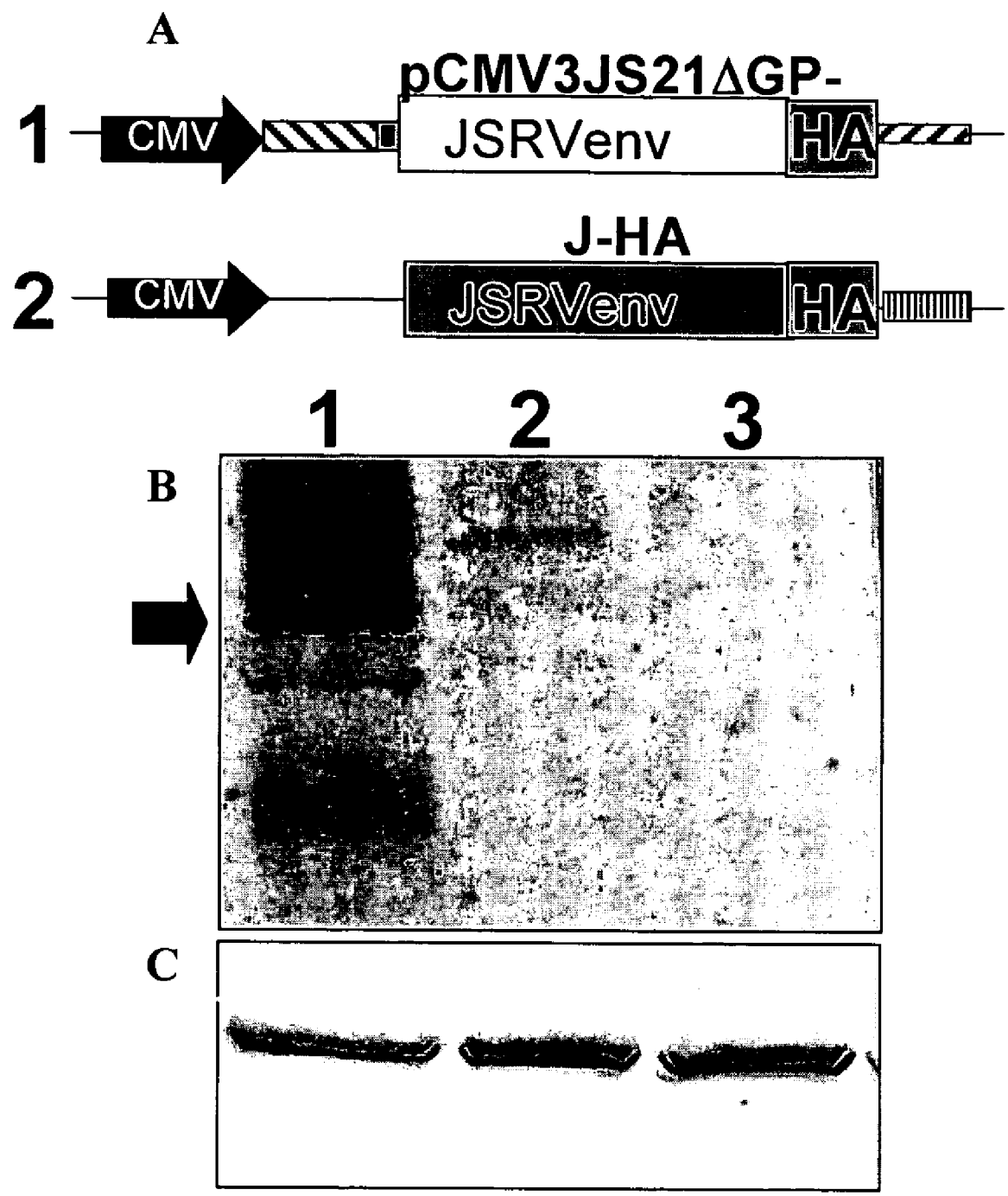
Figures 8A, 8B, 8C, 8D:
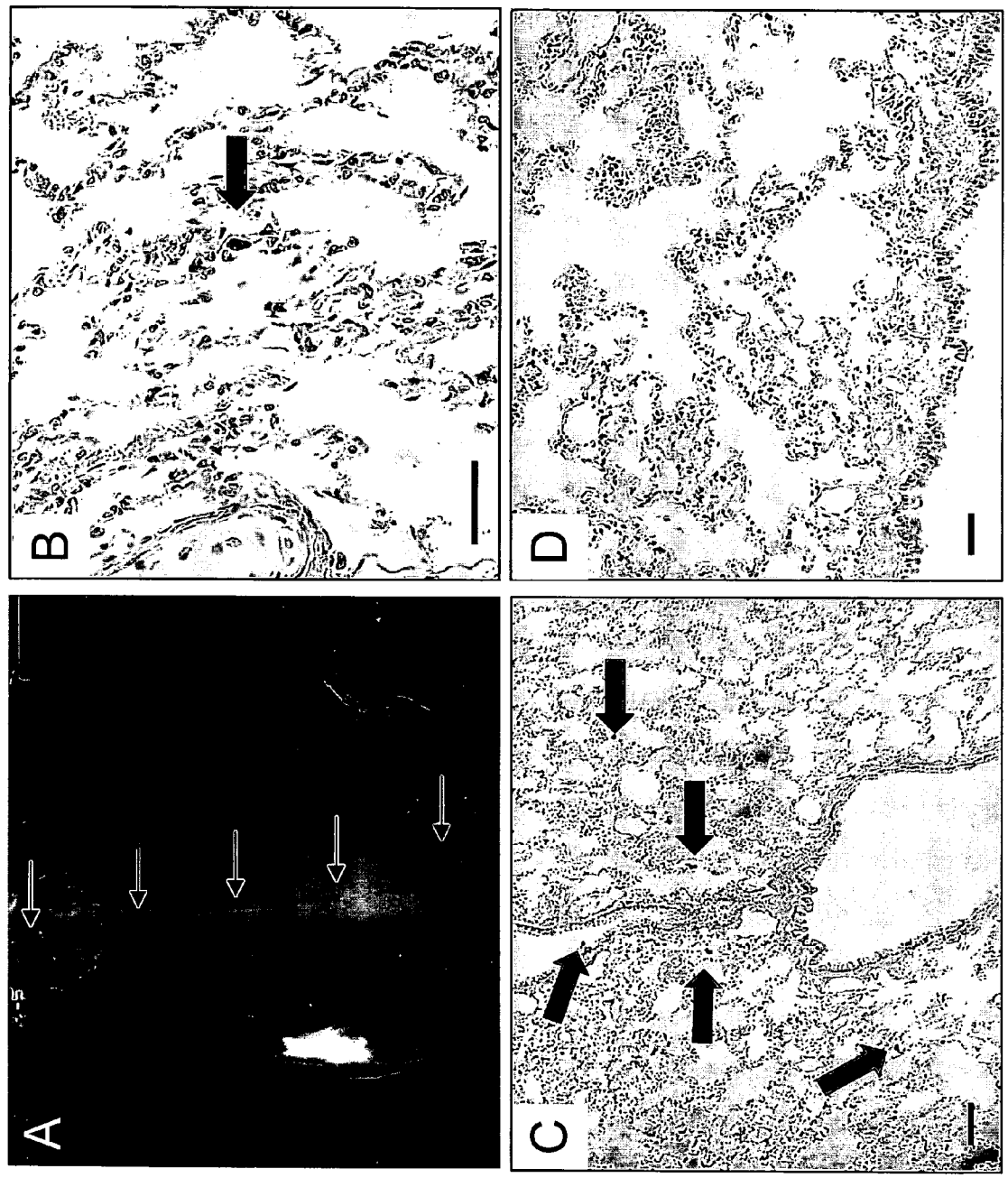

To confirm that increased levels of RNA lead to increased protein production, the pCMV3JS21ΔGP and J constructs were HA tagged at the C-terminus (FIG. 6A). Protein levels were tested using western blot assay of lysates from 293T cells transiently transfected with each construct and a mock transfection control (FIG. 6B). Consistent with RNA data, HA tagged JSRV envelope protein was readily detectable from the pCMV3JS21ΔGP construct but not the J construct (FIG. 6B), whereas the human actin protein levels remained constant (FIG. 6C). RNA levels from the HA-tagged constructs following transient transfection were not statistically different than their untagged counterparts (data not shown).

Figures 7A, 7B:
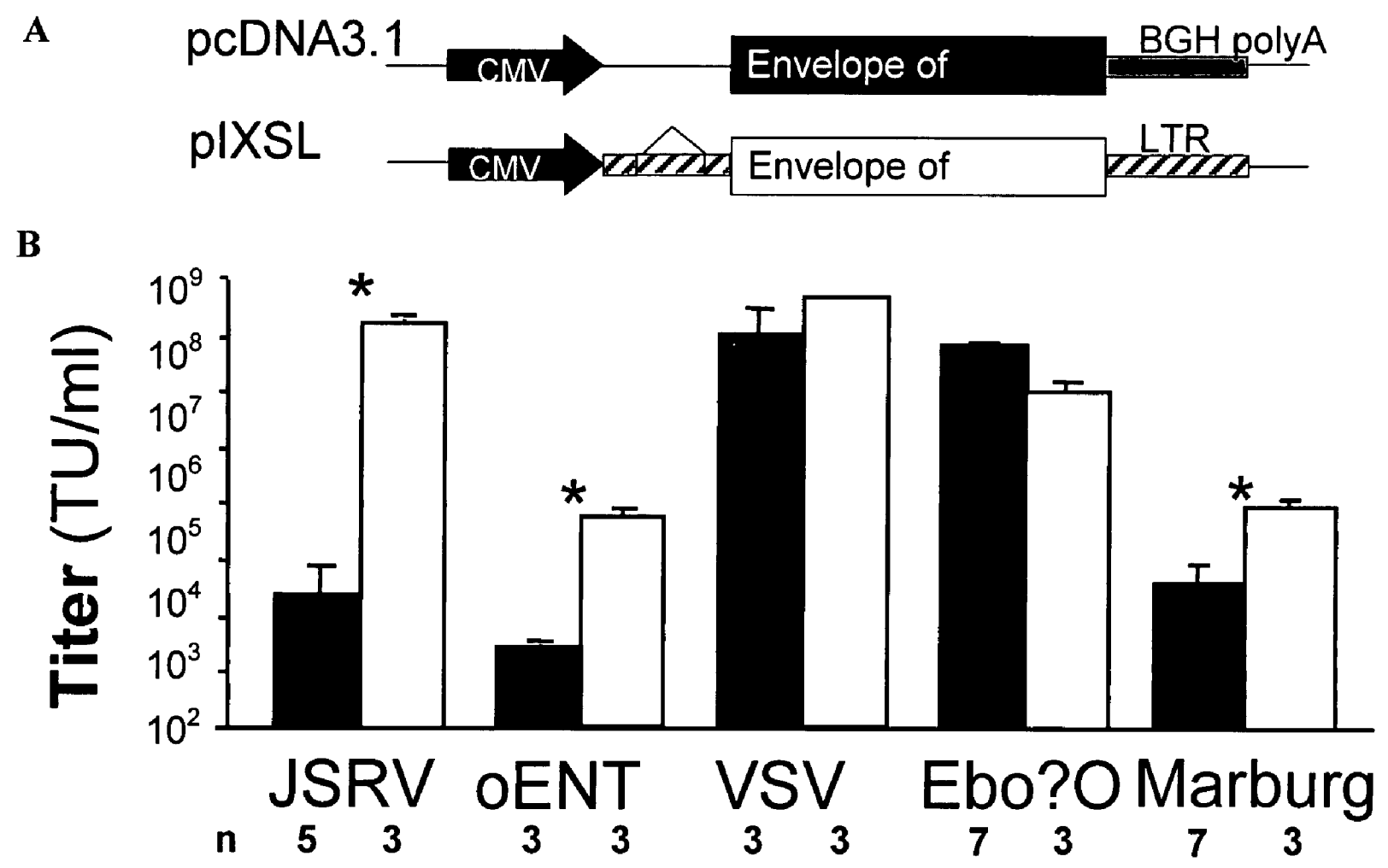

To determine if enhancing elements flanking the JSRV env could be generalized for pseudotyping with other env glycoproteins, an expression construct (termed "pIXSL") was generated in which the JSRV env coding region of 5'J3' was replaced with a multiple cloning site. When either the Marburg or ovine enzootic nasal tumor virus (oENTV) env GPs were expressed from the pIXSL expression plasmid to produce pseudotyped FIV, significant increases in vector titer resulted (FIGS. 7A-7B). Based on these data, the inventors conclude that the JSRV flanking regions confer titer enhancing properties to envelopes with low pseudotyping efficiency. When VSV or EboΔO env cDNAs were expressed from the pIXSL plasmid, no significant differences were observed when compared to pcDNA3.1. These data suggest that the limitation of vector titers that already exceed $10^8$ TU/ml may not be the availability of env RNA for translation. Importantly, when the JSRV env coding region was replaced into the multiple cloning site of pIXSL, a >10,000-fold difference in vector titer between the two expression plasmids was observed (FIGS. 7A-7B), consistent with previous observations (FIG. 1). However, of all the env GPs tested, the effects on the JSRV env were the most pronounced. This suggests that enhancing cis-acting elements present in the flanking regions exert specific interactions with elements within the JSRV env coding region. This observation may have implications for designing optimal expression plasmids for many different species of envelope glycoproteins for the purpose of pseudotyping. For example, the use of analogous oENTV proviral regions to enhance FIV pseudotyping efficiency with oENTV env GP is possible.

The JSRV envelope has been implicated as the causative agent of oncogenic transformation resulting from infection with wild-type JSRV. In this study the inventors demonstrated that efficient pseudotyping of FIV results when the JSRV envelope expression plasmid retains the JSRV 3'LTR, and portions of the JSRV 5'LTR, gag, and pol regions. These findings raise potential biosafety concerns for the use of this vector for gene therapy applications. However, to date there is no data indicating that transduction of cells with a JSRV pseudotyped retroviral vector is sufficient to induce transformation. Overexpression of JSRV env protein either from a transfected expression plasmid or integration of the WT JSRV may be required for oncogenic transformation; in contrast, transient delivery of JSRV protein (as in the case of pseudotyped FIV) may not be sufficient. For an additional margin of safety, one can use mutant JSRV envelope proteins. It has been shown that mutation of a tyrosine residue in the cytoplasmic tail of the transmembrane (TM) domain of JSRV Env protein (Y590D) abolished transformation of rodent fibroblasts, but this mutant envelope protein was capable of pseudotyping MuLV-based vectors (Palmarini et al. 2001).

To rule out the possibility that pseudotyping FIV with the J, 5'J, J3' or 5'J3' env constructs may lead to the generation of replication competent retrovirus (RCR), a real-time PCR based RCR assay (F-PERT) was conducted (Lovatt et al., 1999). All samples were found to be RCR negative (data not shown). This was expected, since it would have been very unlikely that the JSRV env mRNA encoded by AGP would have been packaged into the vector particles, which is a prerequisite for formation of RCRs, for two reasons. First, the JSRV Env expression plasmids were based on pCMV3JS21ΔGP, which deleted all of gag, pro and pol beginning immediately downstream of the splice donor site upstream of gag (nt 355) and ending immediately upstream of the env splice acceptor site (nt 5268). This very likely removed most or all of the RNA packaging signal (ψ), judging from the location of the Ψ sequences in other retroviruses. Second, retroviral RNA packaging is dependent on specific interactions between viral Gag protein and RNA structures, and is generally quite specific. It seems unlikely that even if JSRV RNA contained a packaging signal for JSRV Gag protein that it would be encapsidated by FIV Gag protein.

The low pseudotyping efficiency of some envelope glycoproteins may be due (in part) to low levels of envelope RNA that are available for translation. Increased pseudotyping efficiency may be achieved by expressing the envelope from an efficient expression plasmid or by reintroducing deleted proviral cis-acting elements. Furthermore, these findings indicate that optimization of the envelope expression plasmid can profoundly influence vector titer and should be considered when optimizing vector production for gene transfer applications.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,659,774
U.S. Pat. No. 4,682,195
U.S. Pat. No. 4,683,202
U.S. Pat. No. 4,816,571
U.S. Pat. No. 4,959,463
U.S. Pat. No. 5,141,813
U.S. Pat. No. 5,264,566
U.S. Pat. No. 5,359,046
U.S. Pat. No. 5,428,148
U.S. Pat. No. 5,432,260
U.S. Pat. No. 5,554,744
U.S. Pat. No. 5,574,146
U.S. Pat. No. 5,602,244
U.S. Pat. No. 5,643,756
U.S. Pat. No. 5,645,897
U.S. Pat. No. 5,693,509
U.S. Pat. No. 5,705,629
U.S. Pat. No. 5,849,718
U.S. Pat. No. 5,871,727
U.S. Pat. No. 5,902,584
Arcone et al., *Nucleic Acids Res.*, 16(8):3195-3207, 1988.
Baichwal and Sugden, In: *Gene Transfer*, Kucherlapati (ed.), NY, Plenum Press, 117-148, 1986.
Bedzyk et al., *J. Biol. Chem.*, 265(30):18615-18620, 1990.
Boyes and Bird, *Cell*, 64:1123-1134, 1991.
Burns et al., *Proc. Natl. Acad. Sci. USA*, 90:8033-8037, 1993.
Carter and Flotte, *Curr. Top Microbiol. Immunol.*, 218:119-144, 1996.
Challita et al., *J. Virol.*, 69:748-755, 1995.
Chaudhary et al., *Proc. Natl. Acad. Sci. USA*, 87(3):1066-1070, 1990.
Chen and Okayama, *Mol. Cell Biol.*, 7(8):2745-2752, 1987.
Cosset et al., *J. Virol.*, 69, 7430-7436, 1995.
Coupar et al., *Gene*, 68:1-10, 1988.
Cousens et al., *J. Virol.*, 73(5):3986-3993, 1999.
Davis et al., In: *Microbiology*, 4th ed., Lippincott Co., Philadelphia, 1123-1151, 1990.
EP 266 032
Fechheimer et al., *Proc. Natl. Acad. Sci. USA*, 84:8463-8467, 1987.
Ferrari et al., *J. Virol.*, 70(5):3227-3234, 1996.
Field's Virology, 4th Ed., David M. Knipe. Publisher, Lippincott., 2001.
Fisher et al., *Hum. Gene Ther.*, 7(17):2079-2087, 1996.
Flotte et al., *Proc. Natl. Acad. Sci. USA*, 90(22):10613-10617, 1993.
Fraley et al., *Proc. Natl. Acad. Sci. USA*, 76:3348-3352, 1979.
Froehler et al., *Nucleic Acids Res.*, 14(13):5399-5407, 1986.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gilliland et al., *Proc. Natl. Acad. Sci. USA*, 77(8):4539-4543, 1980.
Glick and Pasternak, In: *Molec. Biotech.*, American Society for Microbiology, Washington, D.C., 412, 1994.
Goodman et al., *Blood*, 84(5):1492-1500, 1994.
Gopal, *Mol. Cell Biol.*, 5:1188-1190, 1985.
Gordon and Anderson, *Curr. Op. Biotechnol.*, 5:611-616, 1994.
Gossen and Bujard, *Proc. Natl. Acad. Sci. USA*, 89(12):5547-5551, 1992.
Gossen et al., *Science*, 268(5218):1766-1769, 1995.
Graham and Van Der Eb, *Virology*, 52:456-467, 1973.
Hara et al., *Gene Ther.*, 2(10):784-788, 1995.
Harland and Weintraub, *J. Cell Biol.*, 101:1094-1099, 1985.
Izaurralde, Eur. *J. Cell Biol.*, 81(11):577-584, 2002.
Jeffers et al., *J. Virol.*, 76(24):12463-12472, 2002.
Johnston et al. *J. Virol.*, 73(3):2491-2498, 1999.
Johnston et al., *J. Virol.*, 73(6):4991-5000, 1999.
Kageyama et al, *J. Biol. Chem.*, 262(5):2345-2351, 1987.
Kaneda et al., *Science*, 243:375-378, 1989.
Kaplitt et al., *Nat. Genet.*, 8(2):148-154, 1994.
Kato et al, *J. Biol. Chem.*, 266:3361-3364, 1991.
Kessler et al., *Proc. Natl. Acad. Sci. USA*, 93(24):14082-14087, 1996.
Klein et al., *Nature*, 327:70, 1987.
Koeberl et al., *Proc. Natl. Acad. Sci. USA*, 94(4):1426-1431, 1997.
Kotani et al., *Human Gene Ther.*, 5:19-28, 1994.
Kyte and Doolittle, *J Mol Biol*, 157(1):105-32, 1982.
Lam et al., *Human Gene Ther.*, 7:1415-1422, 1996.
Lee et al., *Gene Anal Tech.*, 5(2):22-31, 1988.
Lever, *Gene Therapy*, 3:470-471, 1996.
Loh et al., *J. Virol.*, 62:4086-4095, 1988.
Lovatt et al., *J. Virol. Methods*, 82(2):185-200, 1999.
Macejak and Sarnow, *Nature*, 353:90-94, 1991.
Maeda et al., *Cancer Gene Ther.*, 8(11):890-896, 2001.
Markowitz et al., *J. Virol.*, 62:1120-1124, 1988.
McCown et al., *Brain Res*, 713(1-2):99-107, 1996.
Miller and Buttimore, *Mol. Cell Biol.*, 6(8):2895-902, 1986.
Miller and Chen, *J. Virol.*, 70, 5564-5571, 1996.

Miller and Rosman, *Biotechniques*, 7:980-990, 1989.
Miller et al., *Meth. Enzymol.*, 217:581-599, 1993.
Miller et al., *Mol. Cell. Biol.*, 10:4239, 1990.
Miller, *Nature*, 357: 455, 1992.
Mizukami et al., *Virology*, 217(1):124-130, 1996.
Moritz et al., *Blood*, 88:855-862, 1996.
Nicolas and Rubenstein, In: Vectors: *A survey of molecular cloning vectors and their uses*, Rodriguez and Denhardt (Eds.), Stoneham: Butterworth, 493-513, 1988.
Nicolau and Sene, *Biochim. Biophys. Acta*, 721:185-190, 1982.
Nicolau et al., *Methods Enzymol.*, 149:157-176, 1987.
Nienhuis et al., In: *Viruses and Bone Marrow*, Hematology, Young, Ed., 16:353-414 1993.
Oliviero et al., *EMBO J.*, 6(7):1905-1912, 1987.
Palmarini et al., *J. Virol.*, 73:6964-6972, 1999.
Palmarini et al., *J. Virol.*, 75(22):11002-11009, 2001.
Palmarini et al., *Virology*, 294(1):180-188, 2002.
PCT Appl. WO 01/04266
PCT Appl. WO 98/0748
Pelletier and Sonenberg, *Nature*, 334:320-325, 1988.
Ping et al., *Microcirculation*, 3(2):225-228, 1996.
Poli and Cortese, *Proc. Natl. Acad. Sci. USA*, 86(21):8202-8206, 1989.
Potter et al., *Proc. Nat. Acad. Sci. USA*, 81:7161-7165, 1984.
Prowse and Baumann, *Mol. Cell Biol.*, 8(1):42-51, 1988.
Radler et al., *Science*, 275:810-814, 1997.
Rai et al., *J. Virol.*, 74(10):4698-4704, 2000.
Remington's Pharmaceutical Sciences, 15th ed., pages 1035-1038 and 1570-1580, Mack Publishing Company, Easton, Pa., 1980.
Ridgeway, In: *Vectors: A survey of molecular cloning vectors and their uses*, Stoneham: Butterworth, 467-492, 1988.
Rippe et al., *Mol. Cell Biol.*, 10:689-695, 1990.
Ron et al., *Mol Cell Endocrinol.* 21;74(3):C97-104, 1990.
Ross, *Microbiol. Rev.*, 59(3):423-450, 1995.
Russell and Miller, *J. Virol.*, 70:217-222, 1996.
Sambrook et al., In: *Molecular cloning*, Cold Spring Harbor Laboratory Press, Cold Spring Harbor, N.Y., 2001.
Schwartz et al., *J. Virol.*, 66:150-159, 1992.
Sharp et al., *Arch. Virol.*, 78, 89-95, 1983.
Sinn et al., *J. Virol.*, 77(10):5902-10, 2003.
Spanjer and Scherphof, *Biochim. Biophys. Acta*, 21:734(1): 40-47, 1983.
Subbramanian and Cohen, *J. Virol.*, 68:6831-6835, 1994.
Szyf et al., *Mol. Cell. Biol.*, 10:4396-4400, 1990.
Temin, In: Gene Transfer, Kucherlapati (ed.), NY, Plenum Press, 149-188, 1986.
Trono, *Cell*, 82:189-192, 1995.
Tur-Kaspa et al., *Mol. Cell Biol.*, 6:716-718, 1986.
Wang et al., *J. Clin. Invest.*, 104(11):R55-62, 1999.
Watson et al., In: *Recombinant DNA*, 2d Ed., W. H Freeman and Co., NY, 256-263, 1992.
Wilson et al., *Mol. Cell Biol.*, 10(12):6181-6191, 1990.
Wong-Staal, *Microbiol. Rev.*, 55:193-205, 1991.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Xiao, et al., *J. Virol.*, 70:8098-8108, 1996.
Yang et al., *Proc Natl. Acad Sci. USA*, 87:9568-9572, 1990.
Zechner et al., *Mol. Cell Biol.*, 8(6):2394-2401, 1988.

What is claimed is:

1. A polynucleotide preparation comprising:
   (a) a pseudotyping expression cassette comprising:
      (i) a first polynucleotide segment comprising a splice acceptor site and encoding all or part of a heterologous env protein;
      (ii) a second polynucleotide segment positioned 5' to the first polynucleotide segment comprising all or part of a retroviral 5' LTR and a splice donor site; and
      (iii) a third polynucleotide segment positioned 3' to the first polynucleotide segment comprising all or part of a retroviral 3' LTR;
      wherein the pseudotyping expression cassette lacks a GAG and POL encoding nucleic acid sequences; and
   (b) a viral expression vector configured for packaging in a pseudotyped viral particle.

2. The preparation of claim 1, wherein the first polynucleotide segment encodes all or part of a Jaaksiekte sheep retrovirus env protein.

3. The preparation of claim 1, wherein the second polynucleotide segment encodes all or part of a Jaaksiekte sheep retrovirus 5' LTR.

4. The preparation of claim 3, wherein the 5' LTR comprises a R and U5 region.

5. The preparation of claim 3, wherein the 5' LTR comprises a major splice donor site.

6. The preparation of claim 1, wherein the third polynucleotide segment encodes all or part of a Jaaksiekte sheep retrovirus 3' LTR.

7. The preparation of claim 6, wherein the 3' LTR comprises a U3, R, and U5 region.

8. The preparation of claim 1, wherein the pseudotyping expression cassette further comprises a promoter.

9. The preparation of claim 8, wherein the promoter is a CMV IE promoter.

10. The preparation of claim 8, wherein the pseudotyping expression cassette is incorporated into the genome of a cell.

11. The preparation of claim 1, wherein the pseudotyping expression cassette is maintained episomally in a cell.

12. The preparation of claim 1, wherein the viral expression vector is retroviral expression vector.

13. The preparation of claim 12, wherein the retroviral expression vector is a lentiviral expression vector.

14. The preparation of claim 13, wherein the lentiviral expression vector is an immunodeficiency virus expression vector.

15. The preparation of claim 14, wherein the immunodeficiency virus expression vector is a feline immunodeficiency virus expression vector.

16. A viral composition produced by methods comprising:

a) contacting a cell with a pseudotyping expression cassette and a viral vector of claim 1; and b) obtaining a pseudotyped virus produced by the cell.

* * * * *

UNITED STATES PATENT AND TRADEMARK OFFICE
CERTIFICATE OF CORRECTION

| | | |
|---|---|---|
| PATENT NO. | : 7,608,449 B2 | Page 1 of 1 |
| APPLICATION NO. | : 10/845253 | |
| DATED | : October 27, 2009 | |
| INVENTOR(S) | : McCray et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,181 days.

Signed and Sealed this
Twenty-second Day of February, 2011

David J. Kappos
*Director of the United States Patent and Trademark Office*

SEQUENCE LISTING

<160> NUMBER OF SEQ ID NOS: 17

<210> SEQ ID NO 1
<211> LENGTH: 7455
<212> TYPE: DNA
<213> ORGANISM: Ovine pulmonary adenocarcinoma virus

<400> SEQUENCE: 1

```
gcagagtatc agccattttg gtctgatcct ctcaacccca tcttttgtct ctctcttatt      60
ttcttagcga ggacgctccg ttctctccct gtgcaggtgc gactcttgct tgtgctggcc     120
gcggcaggtg gcgcccaacg tggggctcga gctcgacagt tttcttcgcc actactctca     180
ttaattgaaa caagtgagta tatggataaa cgggtgaatt aatttaagga ggagtagtaa     240
ggtatatagt tgagagtata aatatgggac aaacgcatag tcgtcagttg tttgtacaca     300
tgctatctgt aatgttgaaa catagaggga ttactgtttc taaacctaaa ttaattaatt     360
ttctttcatt tattgaggaa gtttgccctt ggttccctag agaaggtaca gtaaatttgg     420
agacatggaa gaaggtagga gaacaaattc ggacgcatta taccttacat ggtcctgaaa     480
aagttcctgt ggaaacttta tccttttgga cattaattcg tgattgcttg gattttgata     540
atgatgaatt gaaacgttta ggaaatttat taaagcagga agaagatcct cttcatactc     600
ccgattcggg acctagttat gatcctcctc ctcctcctcc cccatctctg aaaatgcacc     660
cttcagacaa tgatgattta cttctcttcca cagacgaggc agaactggac gaggaagctg     720
ctaaatacca tcaagaagat tggggttttt tagcacagga aaaaggggca ttaacatcca     780
aagatgagtt ggttgaatgt tttaaaaatc ttactattgc tttacaaaat gcaggaattt     840
```

```
cgcttcctca taataatacc tttccctctg ctccgccttt tcctcccgcc tatactcctt    900
ctgttatggc tggccttgat cccccgcccg ggtttcctcc accgtctaaa catatgtctc    960
ccctacaaag ggcctaaaga caggcacagc gacttggtga agttgtttct gattttctc   1020
ttgcctttcc tgtttttgaa ataacaacc agcgttacta cgaatcactg ccatttaagc   1080
aattaaaaga attaaagatt gcttgttcac aatatggtcc taccgcccca tttaccattg   1140
ctatgataga aaatttgggc actcaagcct tgcccccaaa tgattggaaa cagaccgcta   1200
gggcatgtct ctcaggagga gattatttac tatggaaatc tgagtttttt gaacaatgtg   1260
ctcgtatagc tgatgttaac cgacaacaag gcatacagac ctcttatgaa atgttgattg   1320
gtgaaggtcc ttaccaggct actgatacgc aacttaattt cttacctggt gcgtatgcac   1380
aaatatcaaa tgcggcccga caagcttgga aaaggcttcc tagctccagt actaaaacag   1440
aggatctttc aaaagttcga cagggacctg atgaaccata tcaagatttt gtggcacgac   1500
ttttggatac tataggtaag ataatgtctg atgagaaagc cggaatggta ttagcaaaac   1560
aattggcttt tgaaaatgct aactctgctt gtcaagctgc tttaagacct tatcgaaaaa   1620
agggagatct atctgatttt attcgtattt gtgctgacat tgggccctct tatatgcaag   1680
gtattgctat ggcggcggca ttacagggaa aaagcataaa agaagtactt ttccaacaac   1740
aagctcgaaa taaaaaaggg cttcaaaaat caggtaattc aggttgcttt gtctgtggtc   1800
aacctggcca tcgagctgca gtatgccctc aaaaacaaca aggccctgtt aatacccta   1860
atttatgtcc acgatgtaaa aaaggaaagc attgggcgcg agattgccgt tccaagactg   1920
atgttcaagg taatcctta ccccggttt cgggaaactg ggtgaggggc cagcccctgg   1980
ccccgaaaca atgttatggg gcaacactac aggttccaaa agaaccattg cagacctctg   2040
tcgagccaca agaggcagcg cgggattgga cctctgtgcc acctcctata cagtattaac   2100
tcccgaaatg ggagttcaaa ctcttgctac gggagtgttt gggcctttac ctccagggac   2160
agctggactg cttttagggc gcagcagtgc gtctttaaaa ggaatactta ccatcctgg   2220
tgtgattgac tctgattata caggagagat aaaaatatta gcctccgctc ctaacaaaat   2280
tattgtaatc aatgcaggac agcgtatagc tcaacttctt ttagttccat tagtcataca   2340
aggaaaaaca attaaccgag accgccaaga taaaggtttc gggtcctctg acgcctattg   2400
ggtgcaaaat gttaccgagg cacgaccaga actcgagcta cgcattaatg gtaagctttt   2460
ccgcggagtg cttgatacag gggccgatat tagtgttatt tctgataaat attggcctac   2520
tacatggcca aaacagatgg ctatttccac tctccagggt attggccaaa ctactaatcc   2580
agaacagagt tcatcccttc ttacttggaa ggataaagat ggacatacag gccaatttaa   2640
accctatatt ctgccccatc ttccagttaa tctatggggg cgtgatatat aagcaaaat   2700
gggtgtttat ttatatagtc cttcacccat tgtgacagat tgatgttag atcagggctt   2760
acttccaaat caaggtttag gtaaacaaca tcaaggcatc attttgcccc ttgatttaaa   2820
atctaatcaa gatcgacaag gcttggggtg ttttccttag ggacctctga ttctcctgtg   2880
acacatgccg atcctattga ttggaaatct gaggaaccgg tatgggtcga tcagtggccc   2940
ctaacacagg aaaactttc tgccgcacaa cagctggtgc aggaacagct gagacttggg   3000
catattgaac cctctacctc tgcttggaat tccccaattt ttgttattaa aaagaagtct   3060
gggaaatgga gattgctaca agatcttcgt aaagtaaatg aaacaatgat gcacatggga   3120
gccctacaac ctggggttgcc cactccttct gctatacctg ataagtccta tatcattgtt   3180
```

```
atagatttaa aagattgctt ttacactatt cctcttgcac ctcaagattg caaaagattt    3240
gctttcagtt taccttctgt taattttaaa gagcctatgc aacgctatca atggagagtt    3300
ctcccgcaag gaatgactaa tagccctacg ctgtgccaaa aatttgttgc tacagcaata    3360
gctccggttc gtcaacgttt tcctcagcta tacttggttc attatatgga tgatatatta    3420
ctagctcatg ctgacgaaca tttgttgtat caagcttttt cgattctaaa acaacattta    3480
agtcttaatg gtcttgttat tgccgatgaa aaaattcaga ctcatttccc ttataattat    3540
ttgggtttct ccttatatcc tcgtgtttat aatactcaat tagtaaaact gcagactgac    3600
catttaaaaa ctctaaatga ctttcaaaaa cttttaggag acattaactg gatacgcccg    3660
tatttgaaat tacccactta taccttgcag ccattatttg acattcttaa aggtgactct    3720
gatcctgcat caccccgaac actttcttta gaaggacgaa ctgctttaca atcaatagaa    3780
gaagctatta gacaacaaca gattacttat tgtgattacc aacgatcatg gggtttgtat    3840
atacttccta ccccccgagc acccacaggg gttctctatc aagataaacc tttgcgatgg    3900
atatatctgt ctgctactcc aactaaacat ctgctccctt actatgaact tgttgcaaaa    3960
attgtagcaa agggacgcca cgaggccatc aatattttg gtatggaacc cccctttatt    4020
tgtattcctt atgctttaga acaacaagat tggcttttc aattttcaga caattggtct    4080
atagcttttg caaattaccc gggacagatt actcatcatt atccttccga taaattgtta    4140
caatttgcta gctctcatgc ctttattttt ccaaaagtag ttcgccgaca gcctattccc    4200
gaagcgacac ttatatttac agatggatct tctaatggaa ctgcagcttt aatcattaat    4260
catcaaacct attacgcaca aaccagtttt tcttctgctc aagttgtgga attatttgca    4320
gtccaccaag cgttgctaac tgtacctact tccttcaatt tatttacaga cagctcctat    4380
gtggtcggtg ccttacagat gattgaaact gttccagtta tcggcactac ctctccggaa    4440
gttcttaact tattcacatt gattcaacag gttctccatt gccgccaaca cccctgtttt    4500
tttggacata ttcgtgcaca ttccactctt cctggcgccc tggtacaagg caatcatact    4560
gcggatgttc ttactaaaca aatgtttttt caatcagcta ttgatgcagc ccggaaatcc    4620
catgatttac atcaccaaaa tagtcattct ttacgcttgc aatttaaaat ttctcgtgaa    4680
gctgcacggc aaattgttaa atcttgttct acttgtcctc aattctttgt tctcccctcaa   4740 tatggtgtca accctcgagg tttacgccct aatcacctct ggcaaacaga tgttactcac    4800
attcctcaat ttggacgtct taaatatgtt catgtttcta ttgacacttt ttccaatttt    4860
ctcatggcct ctcttcacac tggagaatct acacgtcact gtattcaaca tttattgttt    4920 tgttttcta cttcaggaat ccctcaaacc cttaagacag ataatggacc tgggtatact    4980
agccgttctt ttcaacgttt ttgtctttct tttcaaattc atcataaaac agggattcct    5040
tataatccac agggacaagg tattgtggaa cgagcccatc aacgccttaa acatcaatta    5100
ttaaaacaaa aaaggggaa tgaattgtat agcccctcac cgcataacgc cttgaaccat    5160
gctctttatg ttttaaattt tttaacttta gacgcagaag gcaattcagc agcccagcga    5220 ttttggggg agcaatcctc atgcaagaaa ccacttgtac gatggaagga tccatttacg    5280
aatctgtggt atgggccaga tcctgtatta atatgggac gagggcatgt tgtgtttttt    5340
ccacagaatg ccgaagcgcc gcgctggatt ccggaaaggc tggtacgcgc ggcagaggaa    5400
ctccctgacg catcaaatgc aacgcatgac gctgagcgag cccacgagtg agctgcccac    5460
ccagaggcaa attgaagcgc taatgcgcta cgcctggaat gaggcacatg tacaacctcc    5520
ggtgacacct actaacatct tgatcatgtt attattattg ttacagcggg tacaaaatgg    5580
```

-continued

```
ggcagctgcg gcttttgggg cgtacattcc tgatccgcca atgattcaat ccttaggatg   5640
ggatagagaa atagtacccg tatatgttaa tgatacgagc cttttaggag gaaaatcaga   5700
tattcacatt tccctcagc aagcaaatat ctcttttat ggccttacca ctcaatatcc     5760
catgtgcttt tcttatcaat cgcagcatcc tcattgtata caggtatcag ctgacatatc   5820
atatcctcga gtgactatct caggcattga tgaaaaaact gggaaaaaat catacgggaa   5880
cggatctgga cccctcgaca ttccgttttg tgacaagcat ttaagcattg cataggcat    5940 agacactcct tggactttat gtcgagcccg gtcgcatca gtatataaca tcaataatgc    6000
caatgccacc ttttatggg attgggcacc tggaggaaca cctgattttc ctgaatatcg    6060
aggacagcat ccgcctattt tctctgtaaa taccgctcca atataccaaa cggaactatg   6120
gaaacttttg gctgcttttg gtcatggcaa tagtttatat ttacagccca atatcagtgg   6180
aagcaaatat ggtgatgtag gagttacagg attttttatat cctcgagctt gcgtgccgta  6240
tccattcatg ttgatacaag gccatatgga ataacactg tcattaaata tttatcattt    6300
gaattgttct aactgcatac tgactaattg tattagggga gtagccaaag gagaacaggt   6360
tataatagta aaacagcctg cctttgtaat gctgcccgtt gaaatagctg aagcctggta   6420
tgatgaaact gctttagaat tattacaacg cattaatacg gctctcagcc gccctaagag   6480
aggcctgagc ctgattattt tgggtatagt atctttaatc accctcatag ctacagctgt   6540
tacggcttcc gtatctttag cacagtctat tcaagctgcg cacacggtag actccttatc   6600
atataatgtt actaaagtga tggggaccca agaagatatt gataaaaaaa tagaagatag   6660
gctatcagct ctatatgatg tagtcagagt cttaggagag caagttcaga gcattaattt   6720
tcgcatgaaa atccaatgtc atgctaacta taaatggatt tgtgttacaa aaaagccata   6780
caatacttct gattttccat gggacaaagt gaagaaacat ttgcaaggaa tttggttcaa   6840
tactaatcta tcgttagacc ttttacaact gcataatgag attcttgata ttgaaaattc   6900
gccgaaggct acactaaata tagccgatac tgttgataat ttcttgcaaa atttattctc   6960 taatttttcct agtctccatt cgctgtggaa aaccctgatt ggtgtaggaa tacttgtgtt   7020
tattataatt gtcgtaatcc ttatatttcc ttgccttgtt cgtggcatgg ttcgcgattt    7080
tctaaagatg agagttgaaa tgctgcatat gaaatataga aatatgttac agcaccaaca   7140
tcttatggag cttttaaaaa ataaagagag gggagatgcg ggggacgacc cgtgaagggt   7200
taagtcctgg gagctctttg gcagaagcca aagcctagga caagtaccta agctccctgt   7260
cccgccaccc tcaagaattt ttaaaagctc ttaaggctcg gatgtttgct tttggcactg   7320
cttcatagaa ataccaggaa atctgattat ataagaatcc ggtgattgtg taagaatccg   7380
gtgggtgtag tgaataatga ataaacaagt tatgtacttt ataaatatag cattgtaata   7440
aagcagagta tcagc                                                    7455
```

<210> SEQ ID NO 2
<211> LENGTH: 1848
<212> TYPE: DNA
<213> ORGANISM: Ovine pulmonary adenocarcinoma virus
<220> FEATURE:
<221> NAME/KEY: CDS
<222> LOCATION: (1)..(1848)

<400> SEQUENCE: 2

```
atg ccg aag cgc cgc gct gga ttc cgg aaa ggc tgg tac gcg cgg cag      48
Met Pro Lys Arg Arg Ala Gly Phe Arg Lys Gly Trp Tyr Ala Arg Gln
  1               5                  10                  15
```

```
agg aac tcc ctg acg cat caa atg caa cgc atg acg ctg agc gag ccc      96
Arg Asn Ser Leu Thr His Gln Met Gln Arg Met Thr Leu Ser Glu Pro
         20                  25                  30 acg agt gag ctg ccc acc cag agg caa att gaa gcg cta atg cgc tac     144
Thr Ser Glu Leu Pro Thr Gln Arg Gln Ile Glu Ala Leu Met Arg Tyr
     35                  40                  45 gcc tgg aat gag gca cat gta caa cct ccg gtg aca cct act aac atc     192
Ala Trp Asn Glu Ala His Val Gln Pro Pro Val Thr Pro Thr Asn Ile
 50                  55                  60 ttg atc atg tta tta tta ttg tta cag cgg gta caa aat ggg gca gct     240
Leu Ile Met Leu Leu Leu Leu Leu Gln Arg Val Gln Asn Gly Ala Ala
 65                  70                  75                  80 gcg gct ttt tgg gcg tac att cct gat ccg cca atg att caa tcc tta     288
Ala Ala Phe Trp Ala Tyr Ile Pro Asp Pro Pro Met Ile Gln Ser Leu
             85                  90                  95 gga tgg gat aga gaa ata gta ccc gta tat gtt aat gat acg agc ctt     336
Gly Trp Asp Arg Glu Ile Val Pro Val Tyr Val Asn Asp Thr Ser Leu
            100                 105                 110 tta gga gga aaa tca gat att cac att tcc cct cag caa gca aat atc     384
Leu Gly Gly Lys Ser Asp Ile His Ile Ser Pro Gln Gln Ala Asn Ile
        115                 120                 125 tct ttt tat ggc ctt acc act caa tat ccc atg tgc ttt tct tat caa     432
Ser Phe Tyr Gly Leu Thr Thr Gln Tyr Pro Met Cys Phe Ser Tyr Gln
    130                 135                 140 tcg cag cat cct cat tgt ata cag gta tca gct gac ata tca tat cct     480
Ser Gln His Pro His Cys Ile Gln Val Ser Ala Asp Ile Ser Tyr Pro
145                 150                 155                 160 cga gtg act atc tca ggc att gat gaa aaa act ggg aaa aaa tca tac     528
Arg Val Thr Ile Ser Gly Ile Asp Glu Lys Thr Gly Lys Lys Ser Tyr
                165                 170                 175 ggg aac gga tct gga ccc ctc gac att ccg ttt tgt gac aag cat tta     576
Gly Asn Gly Ser Gly Pro Leu Asp Ile Pro Phe Cys Asp Lys His Leu
            180                 185                 190 agc att ggc ata ggc ata gac act cct tgg act tta tgt cga gcc cgg     624
Ser Ile Gly Ile Gly Ile Asp Thr Pro Trp Thr Leu Cys Arg Ala Arg
        195                 200                 205 gtc gca tca gta tat aac atc aat aat gcc aat gcc acc ttt tta tgg     672
Val Ala Ser Val Tyr Asn Ile Asn Asn Ala Asn Ala Thr Phe Leu Trp
    210                 215                 220 gat tgg gca cct gga gga aca cct gat ttt cct gaa tat cga gga cag     720
Asp Trp Ala Pro Gly Gly Thr Pro Asp Phe Pro Glu Tyr Arg Gly Gln
225                 230                 235                 240 cat ccg cct att ttc tct gta aat acc gct cca ata tac caa acg gaa     768
His Pro Pro Ile Phe Ser Val Asn Thr Ala Pro Ile Tyr Gln Thr Glu
                245                 250                 255 cta tgg aaa ctt ttg gct gct ttt ggt cat ggc aat agt tta tat tta     816
Leu Trp Lys Leu Leu Ala Ala Phe Gly His Gly Asn Ser Leu Tyr Leu
            260                 265                 270 cag ccc aat atc agt gga agc aaa tat ggt gat gta gga gtt aca gga     864
Gln Pro Asn Ile Ser Gly Ser Lys Tyr Gly Asp Val Gly Val Thr Gly
        275                 280                 285 ttt tta tat cct cga gct tgc gtg ccg tat cca ttc atg ttg ata caa     912
Phe Leu Tyr Pro Arg Ala Cys Val Pro Tyr Pro Phe Met Leu Ile Gln
    290                 295                 300 ggc cat atg gaa ata aca ctg tca tta aat att tat cat ttg aat tgt     960
Gly His Met Glu Ile Thr Leu Ser Leu Asn Ile Tyr His Leu Asn Cys
305                 310                 315                 320 tct aac tgc ata ctg act aat tgt att agg gga gta gcc aaa gga gaa    1008
Ser Asn Cys Ile Leu Thr Asn Cys Ile Arg Gly Val Ala Lys Gly Glu
```

```
                        325                 330                 335
cag gtt ata ata gta aaa cag cct gcc ttt gta atg ctg ccc gtt gaa      1056
Gln Val Ile Ile Val Lys Gln Pro Ala Phe Val Met Leu Pro Val Glu
                340                 345                 350 ata gct gaa gcc tgg tat gat gaa act gct tta gaa tta tta caa cgc      1104
Ile Ala Glu Ala Trp Tyr Asp Glu Thr Ala Leu Glu Leu Leu Gln Arg
            355                 360                 365 att aat acg gct ctc agc cgc cct aag aga ggc ctg agc ctg att att      1152
Ile Asn Thr Ala Leu Ser Arg Pro Lys Arg Gly Leu Ser Leu Ile Ile
        370                 375                 380 ttg ggt ata gta tct tta atc acc ctc ata gct aca gct gtt acg gct      1200
Leu Gly Ile Val Ser Leu Ile Thr Leu Ile Ala Thr Ala Val Thr Ala
385                 390                 395                 400 tcc gta tct tta gca cag tct att caa gct gcg cac acg gta gac tcc      1248
Ser Val Ser Leu Ala Gln Ser Ile Gln Ala Ala His Thr Val Asp Ser
                405                 410                 415 tta tca tat aat gtt act aaa gtg atg ggg acc caa gaa gat att gat      1296
Leu Ser Tyr Asn Val Thr Lys Val Met Gly Thr Gln Glu Asp Ile Asp
            420                 425                 430 aaa aaa ata gaa gat agg cta tca gct cta tat gat gta gtc aga gtc      1344
Lys Lys Ile Glu Asp Arg Leu Ser Ala Leu Tyr Asp Val Val Arg Val
        435                 440                 445 tta gga gag caa gtt cag agc att aat ttt cgc atg aaa atc caa tgt      1392
Leu Gly Glu Gln Val Gln Ser Ile Asn Phe Arg Met Lys Ile Gln Cys
450                 455                 460 cat gct aac tat aaa tgg att tgt gtt aca aaa aag cca tac aat act      1440
His Ala Asn Tyr Lys Trp Ile Cys Val Thr Lys Lys Pro Tyr Asn Thr
                470                 475                 480
465 tct gat ttt cca tgg gac aaa gtg aag aaa cat ttg caa gga att tgg      1488
Ser Asp Phe Pro Trp Asp Lys Val Lys Lys His Leu Gln Gly Ile Trp
            485                 490                 495 ttc aat act aat cta tcg tta gac ctt tta caa ctg cat aat gag att      1536
Phe Asn Thr Asn Leu Ser Leu Asp Leu Leu Gln Leu His Asn Glu Ile
        500                 505                 510 ctt gat att gaa aat tcg ccg aag gct aca cta aat ata gcc gat act      1584
Leu Asp Ile Glu Asn Ser Pro Lys Ala Thr Leu Asn Ile Ala Asp Thr
    515                 520                 525 gtt gat aat ttc ttg caa aat tta ttc tct aat ttt cct agt ctc cat      1632
Val Asp Asn Phe Leu Gln Asn Leu Phe Ser Asn Phe Pro Ser Leu His
530                 535                 540 tcg ctg tgg aaa acc ctg att ggt gta gga ata ctt gtg ttt att ata      1680
Ser Leu Trp Lys Thr Leu Ile Gly Val Gly Ile Leu Val Phe Ile Ile
545                 550                 555                 560 att gtc gta atc ctt ata ttt cct tgc ctt gtt cgt ggc atg gtt cgc      1728
Ile Val Val Ile Leu Ile Phe Pro Cys Leu Val Arg Gly Met Val Arg
                565                 570                 575 gat ttt cta aag atg aga gtt gaa atg ctg cat atg aaa tat aga aat      1776
Asp Phe Leu Lys Met Arg Val Glu Met Leu His Met Lys Tyr Arg Asn
            580                 585                 590 atg tta cag cac caa cat ctt atg gag ctt tta aaa aat aaa gag agg      1824
Met Leu Gln His Gln His Leu Met Glu Leu Leu Lys Asn Lys Glu Arg
        595                 600                 605 gga gat gcg ggg gac gac ccg tga                                      1848
Gly Asp Ala Gly Asp Asp Pro
    610                 615

<210> SEQ ID NO 3
<211> LENGTH: 615
<212> TYPE: PRT
<213> ORGANISM: Ovine pulmonary adenocarcinoma virus
```

<400> SEQUENCE: 3

```
Met Pro Lys Arg Arg Ala Gly Phe Arg Lys Gly Trp Tyr Ala Arg Gln
  1               5                  10                  15

Arg Asn Ser Leu Thr His Gln Met Gln Arg Met Thr Leu Ser Glu Pro
             20                  25                  30

Thr Ser Glu Leu Pro Thr Gln Arg Gln Ile Glu Ala Leu Met Arg Tyr
         35                  40                  45

Ala Trp Asn Glu Ala His Val Gln Pro Pro Val Thr Pro Thr Asn Ile
     50                  55                  60

Leu Ile Met Leu Leu Leu Leu Gln Arg Val Gln Asn Gly Ala Ala
 65                  70                  75                  80

Ala Ala Phe Trp Ala Tyr Ile Pro Asp Pro Pro Met Ile Gln Ser Leu
                 85                  90                  95

Gly Trp Asp Arg Glu Ile Val Pro Val Tyr Val Asn Asp Thr Ser Leu
                100                 105                 110

Leu Gly Gly Lys Ser Asp Ile His Ile Ser Pro Gln Gln Ala Asn Ile
            115                 120                 125

Ser Phe Tyr Gly Leu Thr Thr Gln Tyr Pro Met Cys Phe Ser Tyr Gln
130                 135                 140

Ser Gln His Pro His Cys Ile Gln Val Ser Ala Asp Ile Ser Tyr Pro
145                 150                 155                 160

Arg Val Thr Ile Ser Gly Ile Asp Glu Lys Thr Gly Lys Lys Ser Tyr
                165                 170                 175

Gly Asn Gly Ser Gly Pro Leu Asp Ile Pro Phe Cys Asp Lys His Leu
            180                 185                 190

Ser Ile Gly Ile Gly Ile Asp Thr Pro Trp Thr Leu Cys Arg Ala Arg
        195                 200                 205

Val Ala Ser Val Tyr Asn Ile Asn Asn Ala Asn Ala Thr Phe Leu Trp
    210                 215                 220

Asp Trp Ala Pro Gly Gly Thr Pro Asp Phe Pro Glu Tyr Arg Gly Gln
225                 230                 235                 240

His Pro Pro Ile Phe Ser Val Asn Thr Ala Pro Ile Tyr Gln Thr Glu
                245                 250                 255

Leu Trp Lys Leu Leu Ala Ala Phe Gly His Gly Asn Ser Leu Tyr Leu
            260                 265                 270

Gln Pro Asn Ile Ser Gly Ser Lys Tyr Gly Asp Val Gly Val Thr Gly
        275                 280                 285

Phe Leu Tyr Pro Arg Ala Cys Val Pro Tyr Pro Phe Met Leu Ile Gln
    290                 295                 300

Gly His Met Glu Ile Thr Leu Ser Leu Asn Ile Tyr His Leu Asn Cys
305                 310                 315                 320

Ser Asn Cys Ile Leu Thr Asn Cys Ile Arg Gly Val Ala Lys Gly Glu
                325                 330                 335

Gln Val Ile Ile Val Lys Gln Pro Ala Phe Val Met Leu Pro Val Glu
            340                 345                 350

Ile Ala Glu Ala Trp Tyr Asp Glu Thr Ala Leu Glu Leu Gln Arg
        355                 360                 365

Ile Asn Thr Ala Leu Ser Arg Pro Lys Arg Gly Leu Ser Leu Ile Ile
    370                 375                 380

Leu Gly Ile Val Ser Leu Ile Thr Leu Ile Ala Thr Ala Val Thr Ala
385                 390                 395                 400

Ser Val Ser Leu Ala Gln Ser Ile Gln Ala Ala His Thr Val Asp Ser
```

-continued

```
                        405                 410                 415
Leu Ser Tyr Asn Val Thr Lys Val Met Gly Thr Gln Glu Asp Ile Asp
        420                 425                 430

Lys Lys Ile Glu Asp Arg Leu Ser Ala Leu Tyr Asp Val Val Arg Val
        435                 440                 445

Leu Gly Glu Gln Val Gln Ser Ile Asn Phe Arg Met Lys Ile Gln Cys
        450                 455                 460

His Ala Asn Tyr Lys Trp Ile Cys Val Thr Lys Lys Pro Tyr Asn Thr
465                 470                 475                 480

Ser Asp Phe Pro Trp Asp Lys Val Lys Lys His Leu Gln Gly Ile Trp
                485                 490                 495

Phe Asn Thr Asn Leu Ser Leu Asp Leu Leu Gln Leu His Asn Glu Ile
            500                 505                 510

Leu Asp Ile Glu Asn Ser Pro Lys Ala Thr Leu Asn Ile Ala Asp Thr
        515                 520                 525

Val Asp Asn Phe Leu Gln Asn Leu Phe Ser Asn Phe Pro Ser Leu His
    530                 535                 540

Ser Leu Trp Lys Thr Leu Ile Gly Val Gly Ile Leu Val Phe Ile Ile
545                 550                 555                 560

Ile Val Val Ile Leu Ile Phe Pro Cys Leu Val Arg Gly Met Val Arg
                565                 570                 575

Asp Phe Leu Lys Met Arg Val Glu Met Leu His Met Lys Tyr Arg Asn
            580                 585                 590

Met Leu Gln His Gln His Leu Met Glu Leu Leu Lys Asn Lys Glu Arg
        595                 600                 605

Gly Asp Ala Gly Asp Asp Pro
    610                 615

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
gcagagtatc agccatttt                                                  19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
tattaatatg gggacgaggg                                                 20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gggtggcggg acaggag                                                    18
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gtaatacgac tcactatagg gc                                          22

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ctcattaatt gaaacgatcg agtatatgg                                   29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
ccatatactc gatcgtttca attaatgag                                   29

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
cccaatacgc aaaccgcctc tcccc                                       25

<210> SEQ ID NO 11
<211> LENGTH: 78
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ggtacttgtc ctaggctttg gcttctgcca aagagctccc aggaattcac ccttctgtgg    60
aaaaacacaa acatgccc                                                  78

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12

-continued

```
atgccgaagc accgcgctgg                                               20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ttaacccttc acgggttgtc cccc                                          24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ggcgcttcgg cattctgtgg                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
ccacccagag gcaaattgaa                                               20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ggtgtcaccg gaggttgtac a                                             21

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
cgctaatgcg ctacgcctgg aatg                                          24
```